US006949929B2

(12) United States Patent
Gray et al.

(10) Patent No.: US 6,949,929 B2
(45) Date of Patent: Sep. 27, 2005

(54) MAGNETIC RESONANCE IMAGING INTERFERENCE IMMUNE DEVICE

(75) Inventors: Robert W. Gray, Rochester, NY (US); Paul G. Simpson, III, Rochester, NY (US); Michael L. Weiner, Webster, NY (US)

(73) Assignee: Biophan Technologies, Inc., West Henrietta, NY (US)

( * ) Notice: Subject to any disclaimer, the term of this patent is extended or adjusted under 35 U.S.C. 154(b) by 0 days.

(21) Appl. No.: 10/780,261

(22) Filed: Feb. 17, 2004

(65) Prior Publication Data

US 2004/0263172 A1 Dec. 30, 2004

Related U.S. Application Data

(60) Provisional application No. 60/482,177, filed on Jun. 24, 2003.

(51) Int. Cl.[7] .................................................. G01V 3/00
(52) U.S. Cl. ........................................ 324/318; 324/322
(58) Field of Search ................................ 324/318, 322, 324/309, 307, 300, 319

(56) References Cited

U.S. PATENT DOCUMENTS 5,235,281 A * 8/1993 Haragashira et al. ....... 324/318
5,278,503 A * 1/1994 Keller et al. ................ 324/318
2003/0083723 A1   5/2003 Wilkenson et al.
2003/0083726 A1   5/2003 Zeijlemaker et al.

OTHER PUBLICATIONS

M.E. Ladd, et. al. "A 0.7mm Triaxial Cable For Significantly Reducing RF Heating In Interventional MR" Proceedings of the International Society of Magnetic Resonance in Medicine, 7 (1999).

"Reduction of Resonant RF Heating in Intravascular Catheters Using Coaxial Chokes" Magnetic Resonance in Medicine, 2000:43:615–619.

* cited by examiner

Primary Examiner—Brij Shrivastav
(74) Attorney, Agent, or Firm—Basch & Nickerson LLP; Michael J. Nickerson

(57) ABSTRACT

A voltage compensation unit reduces the effects of induced voltages upon a device having a single wire line. The single wire line has balanced characteristic impedance. The voltage compensation unit includes a tunable compensation circuit connected to the wire line. The tunable compensation circuit applies supplemental impedance to the wire line. The supplemental impedance causes the characteristic impedance of the wire line to become unbalanced, thereby reducing the effects of induced voltages caused by changing magnetic fields.

49 Claims, 11 Drawing Sheets

MAGNETIC RESONANCE IMAGING INTERFERENCE IMMUNE DEVICE

PRIORITY INFORMATION

This application claims priority under 35 U.S.C. §119(e) from U.S. Provisional Patent Application, Ser. No. 60/482, 177, filed on Jun. 24, 2003. The entire content of U.S. Provisional Patent Application, Ser. No. 60/482,177 is hereby incorporated by reference.

CROSS REFERENCE TO RELATED PATENT APPLICATIONS

The subject matter of co-pending U.S. patent application Ser. No. 09/885,867, filed on Jun. 20, 2001, entitled "Controllable, Wearable MRI-Compatible Cardiac Pacemaker With Pulse Carrying Photonic Catheter And VOO Functionality"; co-pending U.S. patent application Ser. No. 09/885,868, filed on Jun. 20, 2001, entitled "Controllable, Wearable MRI-Compatible Cardiac Pacemaker With Power Carrying Photonic Catheter And VOO Functionality"; co-pending U.S. patent application Ser. No. 10/037,513, filed on Jan. 4, 2002, entitled "Optical Pulse Generator For Battery Powered Photonic Pacemakers And Other Light Driven Medical Stimulation Equipment"; co-pending U.S. patent application Ser. No. 10/037,720, filed on Jan. 4, 2002, entitled "Opto-Electric Coupling Device For Photonic Pacemakers. And Other Opto-Electric Medical Stimulation Equipment"; co-pending U.S. patent application Ser. No. 09/943,216, filed on Aug. 30, 2001, entitled "Pulse width Cardiac Pacing Apparatus"; co-pending U.S. patent application Ser. No. 09/964,095, filed on Sep. 26, 2001, entitled "Process for Converting Light"; and co-pending U.S. patent application Ser. No. 09/921,066, filed on Aug. 2, 2001, entitled "MRI-Resistant Implantable Device". The entire contents of each of the above noted co-pending U.S. patent applications (Ser. Nos. 09/885,867; 09/885,868; 10/037,513; 10/037,720; 09/943,216; 09/964,095; and 09/921,066) are hereby incorporated by reference.

FIELD OF THE PRESENT INVENTION

The present invention is directed to a device for protecting a patient, physician, and/or electronic components in an electrical device implanted or partially implanted within the patient. More particularly, the present invention is directed to a device for protecting the conductive parts of the electrical device from current and voltage surges induced by magnetic resonance imaging systems' oscillating magnetic fields.

BACKGROUND OF THE PRESENT INVENTION

Magnetic resonance imaging ("MRI") has been developed as an imaging technique adapted to obtain both images of anatomical features of human patients as well as some aspects of the functional activities and characteristics of biological tissue. These images have medical diagnostic value in determining the state of the health of the tissue examined. Unlike the situation with fluoroscopic imaging, a patient undergoing magnetic resonance imaging procedure may remain in the active imaging system for a significant amount of time, e.g. a half-hour or more, without suffering any adverse effects.

In an MRI process, a patient is typically aligned to place the portion of the patient's anatomy to be examined in the imaging volume of the MRI apparatus. Such an MRI apparatus typically comprises a primary electromagnet for supplying a constant magnetic field ($B_0$) which, by convention, is along the z-axis and is substantially homogeneous over the imaging volume and secondary electromagnets that can provide linear magnetic field gradients along each of three principal Cartesian axes in space (generally x, y, and z, or $x_1$, $x_2$ and $x_3$, respectively). The MRI apparatus also comprises one or more radio frequency coils that provide excitation and detection of the MRI induced signals in the patient's body.

The gradient fields are switched ON and OFF at different rates depending on the MRI scan sequence used. In some cases, this may result in a changing magnetic field on the order of dB/dt=50 T/s. The frequency that a gradient field may be turned ON can be between 200 Hz to about 300 kHz.

For a single loop with a fixed area, Lenz's law can be stated as:

$$EMF=-A \circ dB/dt$$

where A is the area vector, B is the magnetic field vector, and "∘" is the vector scalar product. This equation indicates that an electro-motive-force (EMF) is developed in any loop that encircles a changing magnetic field.

In an MRI system, there is applied to the biological sample (patient) a switched gradient field in all 3 coordinate directions (x-, y-, z-directions). If the patient has an implanted heart pacemaker (or other implanted devices having conductive components) the switched gradient magnetic fields (an alternating magnetic field) may cause:

1. Erroneous signals to be induced/generated in a sensing lead or device or circuit;
2. Damage to electronics; and/or
3. Harmful stimulation of tissue, e.g. heart muscle, nerves, etc.

As noted above, the use of the MRI process with patients who have implanted medical assist devices; such as cardiac assist devices or implanted insulin pumps; often presents problems. As is known to those skilled in the art, implantable devices (such as implantable pulse generators (IPGs) and cardioverter/defibrillator/pacemakers (CDPs)) are sensitive to a variety of forms of electromagnetic interference (EMI) because these enumerated devices include sensing and logic systems that respond to low-level electrical signals emanating from the monitored tissue region of the patient. Since the sensing systems and conductive elements of these implantable devices are responsive to changes in local electromagnetic fields, the implanted devices are vulnerable to external sources of severe electromagnetic noise, and in particular, to electromagnetic fields emitted during the magnetic resonance imaging (MRI) procedure. Thus, patients with implantable devices are generally advised not to undergo magnetic resonance imaging (MRI) procedures.

To more appreciate the problem, the use of implantable cardiac assist devices during a MRI process will be briefly discussed.

The human heart may suffer from two classes of rhythmic disorders or arrhythmias: bradycardia and tachyarrhythmia. Bradycardia occurs when the heart beats too slowly, and may be treated by a common implantable pacemaker delivering low voltage (about 3 V) pacing pulses.

The common implantable pacemaker is usually contained within a hermetically sealed enclosure, in order to protect the operational components of the device from the harsh environment of the body, as well as to protect the body from the device.

The common implantable pacemaker operates in conjunction with one or more electrically conductive leads, adapted to conduct electrical stimulating pulses to sites within the patient's heart, and to communicate sensed signals from those sites back to the implanted device.

Furthermore, the common implantable pacemaker typically has a metal case and a connector block mounted to the metal case that includes receptacles for leads which may be used for electrical stimulation or which may be used for sensing of physiological signals. The battery and the circuitry associated with the common implantable pacemaker are hermetically sealed within the case. Electrical interfaces are employed to connect the leads outside the metal case with the medical device circuitry and the battery inside the metal case.

Electrical interfaces serve the purpose of providing an electrical circuit path extending from the interior of a hermetically sealed metal case to an external point outside the case while maintaining the hermetic seal of the case. A conductive path is provided through the interface by a conductive pin that is electrically insulated from the case itself.

Such interfaces typically include a ferrule that permits attachment of the interface to the case, the conductive pin, and a hermetic glass or ceramic seal that supports the pin within the ferrule and isolates the pin from the metal case.

A common implantable pacemaker can, under some circumstances, be susceptible to electrical interference such that the desired functionality of the pacemaker is impaired. For example, common implantable pacemaker requires protection against electrical interference from electromagnetic interference (EMI), defibrillation pulses, electrostatic discharge, or other generally large voltages or currents generated by other devices external to the medical device. As noted above, more recently, it has become crucial that cardiac assist systems be protected from magnetic-resonance imaging sources.

Such electrical interference can damage the circuitry of the cardiac assist systems or cause interference in the proper operation or functionality of the cardiac assist systems. For example, damage may occur due to high voltages or excessive currents introduced into the cardiac assist system.

Moreover, problems are realized when the placement of the implant is next to particular organs. For example, when a pacemaker is placed in the upper chest and the lead tip is placed into the heart, a loop (an electrical loop) is created. A changing magnetic field (the switched gradient field) over the area of the loop (through the area of the loop) will cause an induced voltage (and current) across the heart. This induced voltage (current) can stimulate the heart inappropriately and can cause heart damage or death.

Therefore, it is desirable to provide a medical device or system that reduces or eliminates the undesirable effects of changing magnetic fields from an MRI system on the medical devices and/or patients undergoing medical procedures or that have temporary or permanent implanted materials and/or devices with conducting components.

SUMMARY OF THE PRESENT INVENTION

A first aspect of the present invention is a voltage compensation unit for reducing the effects of induced voltages upon a device to a safe level. The voltage compensation unit includes a sensing circuit to sense voltages induced in conductive components of the device, the voltages being induced by changing magnetic fields and a compensation circuit, operatively connected to the sensing circuit and responsive thereto, to provide opposing voltages to the device to reduce the effects of induced voltages caused by changing magnetic fields.

A second aspect of the present invention is a voltage compensation unit for reducing the effects of induced voltages upon a tissue invasive medical tool to a safe level. The voltage compensation unit includes a sensing circuit to sense voltages induced in conductive components of the medical tool, the voltages being induced by changing magnetic fields; a compensation circuit, operatively connected to the sensing circuit and responsive thereto, to provide opposing voltages to the medical tool to reduce the effects of induced voltages caused by changing magnetic fields; and a connection device to provide an electrical connection between the sensing circuit and the compensation circuit and the medical tool.

A third aspect of the present invention is a voltage compensation unit for reducing the effects of induced voltages upon a device to a safe level. The voltage compensation unit includes a communication circuit, communicatively linked to a MRI system, to receive information associated with a start and end of an application of changing magnetic fields produced by the MRI system and a compensation circuit, operatively connected to the communication circuit and responsive thereto, to synchronize application of opposing voltages to the device with the sensed changing magnetic fields, the opposing voltages reducing the effects of induced voltages caused by the changing magnetic fields.

A fourth aspect of the present invention is a voltage compensation unit for reducing the effects of induced voltages upon a device to a safe level. The voltage compensation unit includes a communication circuit, communicatively linked to a MRI system, to receive information associated with a start and end of an application of changing magnetic fields produced by the MRI system and a compensation circuit, operatively connected to the communication circuit and responsive thereto, to apply opposing voltages to the device, the opposing voltages reducing the effects of induced voltages caused by the changing magnetic fields.

A fifth aspect of the present invention is a voltage compensation unit for reducing the effects of induced voltages upon a device having a single wire line, the single wire line having a balanced characteristic impedance. The voltage compensation unit includes a tunable compensation circuit, operatively connected to the wire line, to apply supplemental impedance to the wire line, the supplemental impedance causing the characteristic impedance of the wire line to become unbalanced, thereby reducing the effects of induced voltages caused by changing magnetic fields.

Another aspect of the present invention is a system for reducing the effects of MRI induced signals to a safe level. The system includes a medical device wherein the medical device has a housing having electronic circuitry therein, a first lead to provide an electrical path for a stimulation signal generated by the electronic circuitry to be applied to a desired tissue region, a second lead to provide an electrical path for a sensed physiological condition of the desired tissue region to be communicated to the electronic circuitry, and a third lead to provide an electrical ground. The system also includes a diode, operatively connected to the first lead, to significantly reduce MRI induced signals from traveling along the first lead to the electronic circuitry.

A further aspect of the present invention is a system for reducing the effects of MRI induced signals to a safe level. The system includes a MRI system; a medical device; and a transceiver to provide communication between the MRI system and the medical device. The medical device has a housing having electronic circuitry therein, a bi-directional lead to provide an electrical path for a stimulation signal generated by the electronic circuitry to be applied to a desired tissue region and to provide an electrical path for a sensed physiological condition of the desired tissue region to be communicated to the electronic circuitry, and a lead to provide an electrical ground. The medical device indicates to the MRI system, through the transceiver, when the stimulation signal will be applied to the desired tissue region. The MRI system, in response to the indication from the medical device of when the stimulation signal will be applied to the desired tissue region, terminates a production of MRI switched gradient fields.

A further aspect of the present invention is a system for reducing the effects of MRI induced signals to a safe level. The system includes a medical device wherein the medical device has a housing having electronic circuitry therein, and leads to provide an electrical path for a stimulation signal generated by the electronic circuitry to be applied to a desired tissue region and to provide an electrical path for a sensed physiological condition of the desired tissue region to be communicated to the electronic circuitry, a sensor to sense application of switched MRI gradient fields, and an electronic component, operatively connected to the leads, to significantly reduce MRI induced signals from traveling along the leads to the electronic circuitry, and a switch, operatively connected to the sensor and the electronic component, to operatively connect the electronic component to the leads when the sensor senses the application of switched MRI gradient fields and to operatively disconnect the electronic component from the leads when the sensor fails to sense the application of switched MRI gradient fields.

A further aspect of the present invention is an electrical lead component for a medical device that reduces the effects of MRI induced signals to a safe level. The electrical lead component includes a medical device electrical lead capable of providing an electrical path to a desired tissue region and a coil that generates a MRI switched gradient field induced current opposite to that which would be induced by the MRI switched gradient fields in the medical device electrical lead so as to reduce voltages induced by the MRI switched gradient fields to a safe level.

A further aspect of the present invention is an electrical lead component for a medical device that reduces the effects of MRI induced signals to a safe level. The electrical lead component includes a medical device electrical lead capable of providing an electrical path to a desired tissue region and a plurality of coils, each coil generating a MRI switched gradient field induced current such a combination of the MRI switched gradient field induced currents provide a combined current that is opposite to that which would be induced by the MRI switched gradient fields in the medical device electrical lead so as to reduce voltages induced by the MRI switched gradient fields to a safe level.

A further aspect of the present invention is an electrical lead component for a medical device that reduces the effects of MRI induced signals to a safe level. The electrical lead component includes a medical device electrical lead capable of providing an electrical path to a desired tissue region and three orthogonally planar coils, each coil generating a MRI switched gradient field induced current such a combination of the MRI switched gradient field induced currents provide a combined current that is opposite to that which would be induced by the MRI switched gradient fields in the medical device electrical lead so as to reduce voltages induced by the MRI switched gradient fields to a safe level.

A further aspect of the present invention is an electrical lead component for a medical device that reduces the effects of MRI induced signals to a safe level. The electrical lead component includes a medical device electrical lead capable of providing an electrical path to a desired tissue region; a plurality of coils, each coil generating a MRI switched gradient field induced current; a sensor to measure a strength of voltages induced by the MRI switched gradient fields; and a switching device, operatively connected to the sensor and plurality of coils, to operatively connect a number of the plurality of coils in response to the measured strength of voltages induced by the MRI switched gradient fields such that a combination of the MRI switched gradient field induced currents produced by the number of operatively connected switches provide a combined current that is opposite to that which would be induced by the MRI switched gradient fields in the medical device electrical lead so as to reduce voltages induced by the MRI switched gradient fields to a safe level.

A further aspect of the present invention is an electrical lead component for a medical device that reduces the effects of MRI induced signals to a safe level. The electrical lead component includes a medical device electrical lead capable of providing an electrical path to a desired tissue region; three orthogonally planar coils, each coil generating a MRI switched gradient field induced current; a sensor to measure a strength of voltages induced by the MRI switched gradient fields; and a switching device, operatively connected to the sensor and the coils, to operatively connect a number of the coils in response to the measured strength of voltages induced by the MRI switched gradient fields such that a combination of the MRI switched gradient field induced currents produced by the number of operatively connected switches provide a combined current that is opposite to that which would be induced by the MRI switched gradient fields in the medical device electrical lead so as to reduce voltages induced by the MRI switched gradient fields to a safe level.

A further aspect of the present invention is an electrical lead component for a medical device that reduces the effects of MRI induced signals to a safe level. The electrical lead component includes a medical device electrical lead capable of providing an electrical path to a desired tissue region; a plurality of coils, each coil generating a MRI switched gradient field induced current; a transceiver to receive a signal indicating a number of coils to be connected; and a switching device, operatively connected to the transceiver and plurality of coils, to operatively connect a number of the plurality of coils in response to the received signal indicating the number of coils to be connected such that a combination of the MRI switched gradient field induced currents produced by the number of operatively connected switches provide a combined current that is opposite to that which would be induced by the MRI switched gradient fields in the medical device electrical lead so as to reduce voltages induced by the MRI switched gradient fields to a safe level.

A further aspect of the present invention is an electrical lead component for a medical device that reduces the effects of MRI induced signals to a safe level. The electrical lead component includes a medical device electrical lead capable of providing an electrical path to a desired tissue region; three orthogonally planar coils, each coil generating a MRI switched gradient field induced current; a transceiver to receive a signal indicating a number of coils to be connected; and a switching device, operatively connected to the transceiver and the coils, to operatively connect a number of the coils in response to the received signal indicating the number of coils to be connected such that a combination of the MRI switched gradient field induced currents produced by the number of operatively connected switches provide a combined current that is opposite to that which would be induced by the MRI switched gradient fields in the medical device electrical lead so as to reduce voltages induced by the MRI switched gradient fields to a safe level.

A further aspect of the present invention is a medical device that reduces the effects of MRI induced signals to a safe level. The medical device includes a medical device capable of providing medical treatment to a desired tissue region and a coil that generates a MRI switched gradient field induced current opposite to that which would be induced by the MRI switched gradient fields in the medical device so as to reduce voltages induced by the MRI switched gradient fields to a safe level.

A further aspect of the present invention is a medical device that reduces the effects of MRI induced signals to a safe level. The medical device includes a medical device capable of providing medical treatment to a desired tissue region and a plurality of coils, each coil generating a MRI switched gradient field induced current such a combination of the MRI switched gradient field induced currents provide a combined current that is opposite to that which would be induced by the MRI switched gradient fields in the medical device so as to reduce voltages induced by the MRI switched gradient fields to a safe level.

A further aspect of the present invention is a medical device that reduces the effects of MRI induced signals to a safe level. The medical device includes a medical device capable of providing medical treatment to a desired tissue region and three orthogonally planar coils, each coil generating a MRI switched gradient field induced current such a combination of the MRI switched gradient field induced currents provide a combined current that is opposite to that which would be induced by the MRI switched gradient fields in the medical device so as to reduce voltages induced by the MRI switched gradient fields to a safe level.

A further aspect of the present invention is a medical device that reduces the effects of MRI induced signals to a safe level. The medical device includes a medical device capable of providing medical treatment to a desired tissue region; a plurality of coils, each coil generating a MRI switched gradient field induced current; a sensor to measure a strength of voltages induced by the MRI switched gradient fields; and a switching device, operatively connected to the sensor and plurality of coils, to operatively connect a number of the plurality of coils in response to the measured strength of voltages induced by the MRI switched gradient fields such that a combination of the MRI switched gradient field induced currents produced by the number of operatively connected switches provide a combined current that is opposite to that which would be induced by the MRI switched gradient fields in the medical device so as to reduce voltages induced by the MRI switched gradient fields to a safe level.

A further aspect of the present invention is a medical device that reduces the effects of MRI induced signals to a safe level. The medical device includes a medical device capable of providing medical treatment to a desired tissue region; three orthogonally planar coil, each coil generating a MRI switched gradient field induced current; a sensor to measure a strength of voltages induced by the MRI switched gradient fields; and a switching device, operatively connected to the sensor and plurality of coils, to operatively connect a number of the plurality of coils in response to the measured strength of voltages induced by the MRI switched gradient fields such that a combination of the MRI switched gradient field induced currents produced by the number of operatively connected switches provide a combined current that is opposite to that which would be induced by the MRI switched gradient fields in the medical device so as to reduce voltages induced by the MRI switched gradient fields to a safe level.

A further aspect of the present invention is a medical device that reduces the effects of MRI induced signals to a safe level. The medical device includes a medical device capable of providing medical treatment to a desired tissue region; a plurality of coils, each coil generating a MRI switched gradient field induced current; a transceiver to receive a signal indicating a number of coils to be connected; and a switching device, operatively connected to the transceiver and the coils, to operatively connect a number of the coils in response to the received signal indicating the number of coils to be connected such that a combination of the MRI switched gradient field induced currents produced by the number of operatively connected switches provide a combined current that is opposite to that which would be induced by the MRI switched gradient fields in the medical device electrical lead so as to reduce voltages induced by the MRI switched gradient fields to a safe level.

A further aspect of the present invention is a medical device that reduces the effects of MRI induced signals to a safe level. The medical device includes a medical device capable of providing medical treatment to a desired tissue region; three orthogonally planar coil, each coil generating a MRI switched gradient field induced current; a transceiver to receive a signal indicating a number of coils to be connected; and a switching device, operatively connected to the transceiver and the coils, to operatively connect a number of the coils in response to the received signal indicating the number of coils to be connected such that a combination of the MRI switched gradient field induced currents produced by the number of operatively connected switches provide a combined current that is opposite to that which would be induced by the MRI switched gradient fields in the medical device electrical lead so as to reduce voltages induced by the MRI switched gradient fields to a safe level.

A further aspect of the present invention is a voltage control unit that reduces the effects of MRI induced signals upon a medical device to a safe level. The voltage control unit includes a coil that generates a MRI switched gradient field induced current opposite to that which would be induced by the MRI switched gradient fields in the medical device so as to reduce voltages induced by the MRI switched gradient fields to a safe level.

A further aspect of the present invention is a voltage control unit that reduces the effects of MRI induced signals upon a medical device to a safe level. The voltage control unit includes a plurality of coils, each coil generating a MRI switched gradient field induced current such a combination of the MRI switched gradient field induced currents provide a combined current that is opposite to that which would be induced by the MRI switched gradient fields in the medical device so as to reduce voltages induced by the MRI switched gradient fields to a safe level.

A further aspect of the present invention is a voltage control unit that reduces the effects of MRI induced signals upon a medical device to a safe level. The voltage control unit includes three orthogonally planar coils, each coil generating a MRI switched gradient field induced current such a combination of the MRI switched gradient field induced currents provide a combined current that is opposite to that which would be induced by the MRI switched gradient fields in the medical device so as to reduce voltages induced by the MRI switched gradient fields to a safe level.

A further aspect of the present invention is a voltage control unit that reduces the effects of MRI induced signals upon a medical device to a safe level. The voltage control unit includes a plurality of coils, each coil generating a MRI switched gradient field induced current; a sensor to measure a strength of voltages induced by the MRI switched gradient fields; and a switching device, operatively connected to the sensor and plurality of coils, to operatively connect a number of the plurality of coils in response to the measured strength of voltages induced by the MRI switched gradient fields such that a combination of the MRI switched gradient field induced currents produced by the number of operatively connected switches provide a combined current that is opposite to that which would be induced by the MRI switched gradient fields in the medical device so as to reduce voltages induced by the MRI switched gradient fields to a safe level.

A further aspect of the present invention is a voltage control unit that reduces the effects of MRI induced signals upon a medical device to a safe level. The voltage control unit includes three orthogonally planar coil, each coil generating a MRI switched gradient field induced current; a sensor to measure a strength of voltages induced by the MRI switched gradient fields; and a switching device, operatively connected to the sensor and plurality of coils, to operatively connect a number of the plurality of coils in response to the measured strength of voltages induced by the MRI switched gradient fields such that a combination of the MRI switched gradient field induced currents produced by the number of operatively connected switches provide a combined current that is opposite to that which would be induced by the MRI switched gradient fields in the medical device so as to reduce voltages induced by the MRI switched gradient fields to a safe level.

A further aspect of the present invention is a voltage control unit that reduces the effects of MRI induced signals upon a medical device to a safe level. The voltage control unit includes a plurality of coils, each coil generating a MRI switched gradient field induced current; a transceiver to receive a signal indicating a number of coils to be connected; and a switching device, operatively connected to the transceiver and the coils, to operatively connect a number of the coils in response to the received signal indicating the number of coils to be connected such that a combination of the MRI switched gradient field induced currents produced by the number of operatively connected switches provide a combined current that is opposite to that which would be induced by the MRI switched gradient fields in the medical device electrical lead so as to reduce voltages induced by the MRI switched gradient fields to a safe level.

A further aspect of the present invention is a voltage control unit that reduces the effects of MRI induced signals upon a medical device to a safe level. The voltage control unit includes three orthogonally planar coil, each coil generating a MRI switched gradient field induced current; a transceiver to receive a signal indicating a number of coils to be connected; and a switching device, operatively connected to the transceiver and the coils, to operatively connect a number of the coils in response to the received signal indicating the number of coils to be connected such that a combination of the MRI switched gradient field induced currents produced by the number of operatively connected switches provide a combined current that is opposite to that which would be induced by the MRI switched gradient fields in the medical device electrical lead so as to reduce voltages induced by the MRI switched gradient fields to a safe level.

A further aspect of the present invention is a lead for medical applications that reduces the effects of MRI induced signals to a safe level. The lead includes two coiled conductive strands forming a spring-like configuration such that current flows over a surface thereof, through contact points between adjacent loops of the coiled conductive strands, and an insulating coating formed over a portion of the two coiled conductive strands such that an inline inductive element is formed, the current flowing along a curvature of the two coiled conductive strands in the insulating coated portion of two coiled conductive strands.

A further aspect of the present invention is a lead for medical applications that reduces the effects of MRI induced signals to a safe level. The lead includes two coiled conductive strands forming a spring-like configuration such that current flows over a surface thereof, through contact points between adjacent loops of the coiled conductive strands, and an adjustable resistive material formed over a portion of the two coiled conductive strands such that an inline inductive element is formed, the current flowing along a curvature of the two coiled conductive strands in the adjustable resistive material portion of two coiled conductive strands, an inductance of the inline inductive element being adjusted by adjusting the resistive properties of the adjustable resistive material.

A further aspect of the present invention is a voltage compensation unit for reducing the effects of induced voltages upon a medical device to a safe level. The voltage compensation unit includes a connection device to provide an electrical connection to the medical device; a sensing circuit to voltages of conductive components in the medical device; and a compensation circuit, operatively connected to the sensing circuit and responsive thereto, to provide opposing voltages to the medical device to reduce the effects of induced voltages caused by changing magnetic fields.

A further aspect of the present invention is a voltage compensation unit for reducing the effects of induced voltages upon a medical device to a safe level. The voltage compensation unit includes a connection device to provide an electrical connection to the medical device; a sensing circuit to detect changing magnetic fields; and a compensation circuit, operatively connected to the sensing circuit and responsive thereto, to synchronize application of opposing voltages to the medical device with the sensed changing magnetic fields, the opposing voltages reducing the effects of induced voltages caused by the changing magnetic fields.

A further aspect of the present invention is a voltage compensation unit for reducing the effects of induced voltages upon a medical device to a safe level. The voltage compensation unit includes a connection device to provide an electrical connection to the medical device; a communication circuit, communicatively linked to a MRI system, to receive information associated with a start and end of an application of changing magnetic fields produced by the MRI system; and a compensation circuit, operatively connected to the communication circuit and responsive thereto, to synchronize application of opposing voltages to the medical device with the sensed changing magnetic fields, the opposing voltages reducing the effects of induced voltages caused by the changing magnetic fields.

A further aspect of the present invention is a voltage compensation unit for reducing the effects of induced voltages upon a medical device to a safe level. The voltage compensation unit includes a connection device to provide an electrical connection to the medical device; a communication circuit, communicatively linked to a MRI system, to receive information associated with a start and end of an application of changing magnetic fields produced by the MRI system; and a compensation circuit, operatively connected to the communication circuit and responsive thereto, to apply opposing voltages to the medical device, the opposing voltages reducing the effects of induced voltages caused by the changing magnetic fields.

BRIEF DESCRIPTION OF THE DRAWINGS

The present invention may take form in various components and arrangements of components, and in various steps and arrangements of steps. The drawings are only for purposes of illustrating a preferred embodiment and are not to be construed as limiting the present invention, wherein.

DETAILED DESCRIPTION OF THE PRESENT INVENTION

Figure 1:
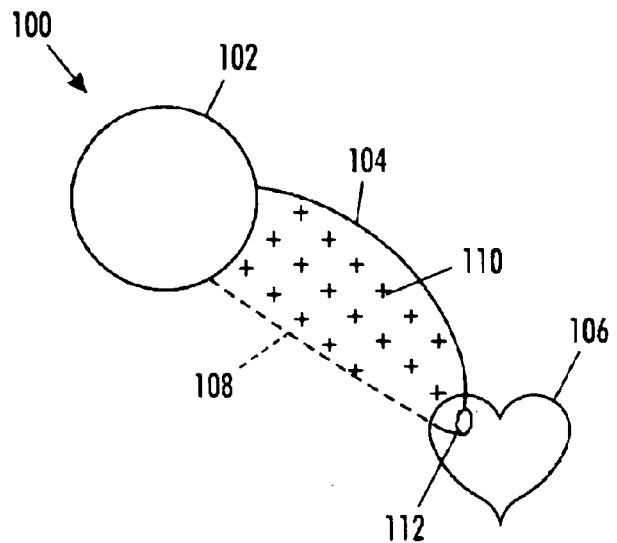
FIG. 1 is a schematic of an implanted pacemaker arrangement in a body.

The present invention will be described in connection with preferred embodiments; however, it will be understood that there is no intent to limit the present invention to the embodiments described herein. On the contrary, the intent is to cover all alternatives, modifications, and equivalents as may be included within the spirit and scope of the present invention as defined by the appended claims.

For a general understanding of the present invention, reference is made to the drawings. In the drawings, like reference have been used throughout to designate identical or equivalent elements. It is also noted that the various drawings illustrating the present invention are not drawn to scale and that certain regions have been purposely drawn disproportionately so that the features and concepts of the present invention could be properly illustrated.

FIG. 1 is a schematic showing a typical pacemaker arrangement 100. The pacemaker comprises a pulse generator canister 102 housing a power supply (not shown) and electronic components (not shown) for sensing and producing electrical pacing pulses. The pulse generator canister 102 has connected to it insulated conductive leads 104 that pass through the body (not shown) and into the heart 106. Conventional bipolar pacemaker leads have two conductive strands, one for pacing and sensing, and the other for ground. The path of the leads 104 is generally not straight. The leads 104 have one or more electrodes 112 in contact with the heart 106. The direct line 108 from the heart 106, where the electrodes 112 are placed, to the generator canister 102 represents a conductive path comprising body tissue (not shown) and fluids (not shown). The completed loop from the pacemaker canister 102, through the leads 104, and back to the pacemaker canister 102 along the path 108 is subject to Lenz's law. That is, a changing magnetic field 110 through the area enclosed by the completed loop (from the pacemaker canister 102, through the leads 104, and back to the pacemaker canister 102 along the path 108) can induce unwanted voltages in the leads 104 and across the heart 106.

In one embodiment of the present invention, and referring to FIG. 1, the pacemaker canister 102 is made out of a non-conductive material. In another embodiment, the canister 102 is coated or covered with various non-conductive insulating materials. This increases the overall resistance of the conductive path loop and thus reduces the voltage across the tissue between electrodes 112 and the canister 102.

Using a three-strand lead design allows for the separation of the pacing signals from the sensing signals and allows for different filtering techniques to be utilized on each separate conductive strand: one strand for the pacing signal for stimulating the heart, one conductive strand for the sensing of the heart's electrical state, pre-pulse, ecg, etc., and one strand for the ground path. Current bi-polar designs use only two conductive strands. This means that the pacing and the sensing signals are carried on the same strand.

For example, in conventional bipolar pacemaker leads, the pacing signal goes "down" (from generator canister to heart) the pacing lead (conductive strand) while the sensing signal travels "up" (from heart to generator canister) the pacing lead. This is the "standard" bipolar pacing setup. If a filter is added to the pacing/sensing strand to block the switch gradient induced signal caused by a MRI system, the pacing pulse/signal must travel through the filter, thereby distorting the pacing pulse.

According to the concepts of the present invention, by adding a third conductive strand, a diode, for example, can be put on the pacing strand and one or more filters can be put on the sensing strand. The filters on the sensing lead may be at the distal end of the pacemaker lead or in the generator canister. Thus, by using separate strands, the present invention is able to utilize different kinds of filters (radio-frequency filters, high/low pass filters, notch filters, etc.) or other electronics in conjunction with each strand depending on the different signal characteristics and/or signal direction along the conductive strand.

Figure 2:
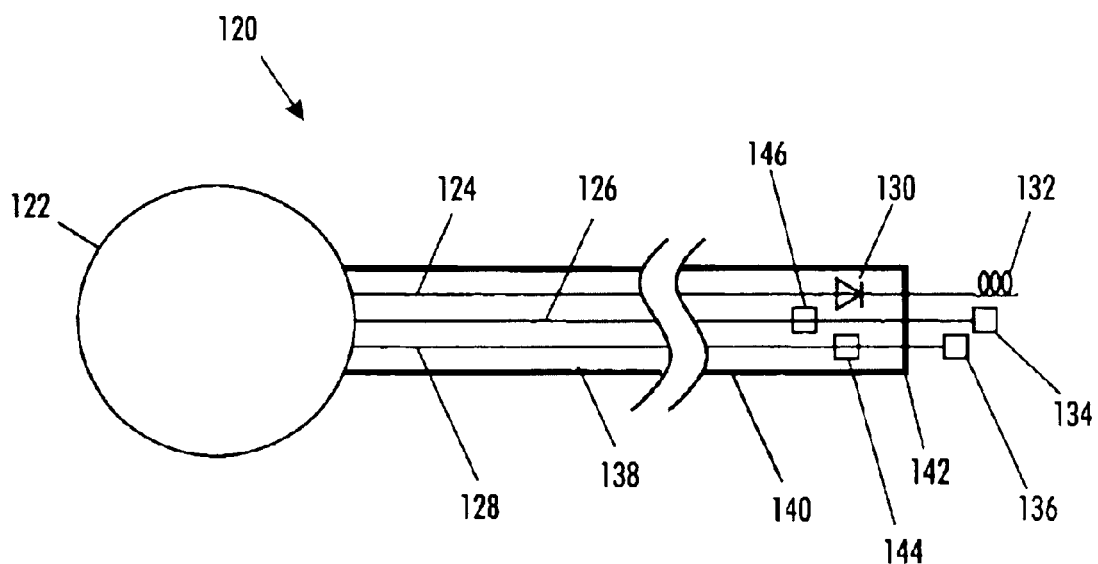
FIG. 2 is a schematic of a pacemaker lead comprising three conductive strands.

FIG. 2 shows a schematic of a pacemaker arrangement 120 including a generator canister 122 containing a pacing pulse generator (not shown), sensing electronics (not shown) and other electronic components (not shown). Attached to the generator canister 122 is a lead assembly 140 having three conductive strands 124, 126, and 128 through lumen 138. Each of the conductive strands 124, 126, and 128 pass through the distal tip 142 of the lead assembly 140 to exposed electrodes 132, 134, and 136, respectively. The exposed electrodes 132, 134, and 136 are placed in contact with or next to the heart.

Conductive strand 124 and electrode 132 are used to deliver pulses to the heart from a pacing generator within the canister 122. Conductive strand 126 and electrode 134 are used as a ground. Conductive strand 128 and electrode 136 are utilized for sensing the electrical signals generated by the heart. In this way, the sensing functionality of pacemakers can be separated from the delivery of pacing pulses.

To block any induced voltage signals from the MRI system's changing magnetic fields (the radio-frequency or the gradient fields) from propagating along the conductive pulse delivery strand 124, a diode 130 is inserted into the conductive strand 124 near the distal tip of the lead assembly 142. It is noted that the diode 130 can also be is placed in the generator canister 122.

With respect to FIG. 2, other electronic components (i.e. radio-frequency chocks, notch filters, etc.) may be placed into the other conductive strands 126 and 128 shown as by components 146 and 144, respectively. It is noted that these optional electronic components 146 and 144 can be placed in the generator canister 122.

Optional electronic components 146 and 144 are used to block or significantly reduce any unwanted induced signals caused by the MRI system from passing along conductive strands 126 and 128 respectively while allowing the desired sensing signals from the heart to pass along conductive strand 126 to electronics in the generator canister 122.

Figure 3:
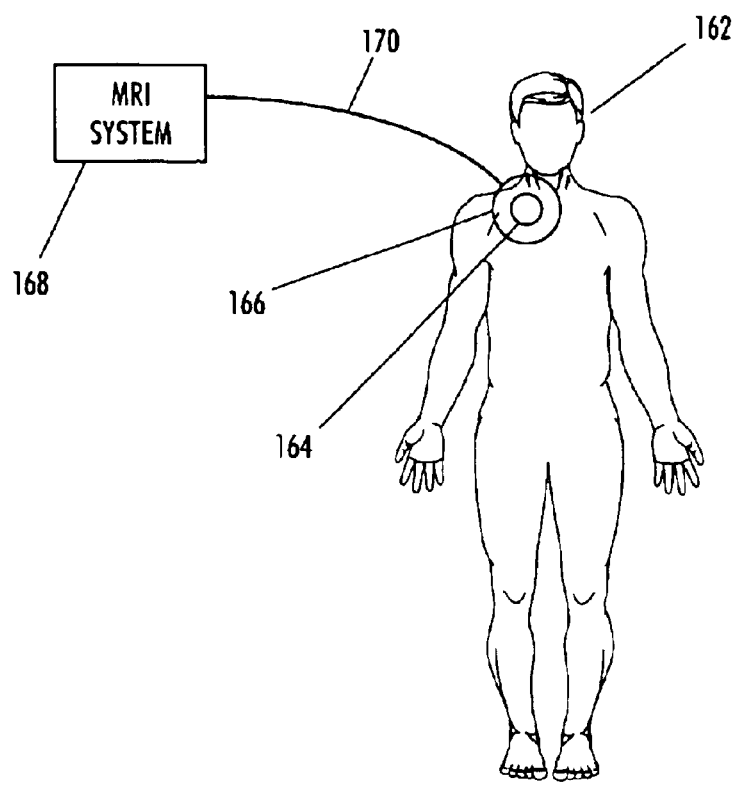
FIG. 3 is a schematic of a sensing system used with a pacemaker.

FIG. 3 is a schematic of an embodiment of the present invention. As illustrated in FIG. 3, a patient 162 is located within an MRI system 168, wherein the patient 162 has an implanted heart pacemaker pulse generator canister 164. A surface sensor/transceiver 166 is placed on the exterior of the patient's body 162 over or near the location of the implanted pacemaker generator 164. The sensor/transceiver 166 is in communication with the MRI system 168 via communication line 170, which may be an MRI safe cable such as a fiber optical cable. Additionally, the sensor/transceiver 166 is in communication with the implanted pacemaker pulse generator canister 164. The means of communication between the sensor/transceiver 166 and the implanted pacemaker generator 164 may be acoustic, optical, or other means that do not interfere with the imaging capabilities or image quality of the MRI system. The signals may be digital or analog.

Moreover, with respect to this embodiment of the present invention, a transmitter/receiver is placed in the pacemaker canister 164 so that the MRI system 168 can be in operative communication with the pacemaker system and vice versa. Thus, the pacing system can transmit signals to the MRI system 168 indicating when the pacemaker is about to deliver a pacing pulse to the heart. The transmitted signals may be digital or analog. In response to this transmitted signal, the MRI system 168 stops or pauses the MRI switched gradient field (imaging scanning sequence) to allow the pacing pulse to occur. After the pacing pulse has been delivered to the heart, the MRI system 168 resumes or begins a new imaging scanning sequence.

In another mode of operation, the MRI system 168 sends signals to the implanted heart pacemaker pulse generator canister 164 through the sensor/transceiver 166 indicating the application of switched gradient fields. The pacemaker may use this information to switch filters or other electronics in and out of the circuit to reduce or eliminate voltages induced in the pacemaker leads by the gradient fields. For example, the pacemaker may switch in additional resistance or inductance or impedance into the pacing/sensing and/or ground strands based on the signal from the MRI system 168 signifying the application of the gradient fields.

In another configuration, there is no surface sensor/transceiver or communication line to the MRI system 168. Instead, there is a special sensor in the implanted heart pacemaker pulse generator canister 164 that can sense the application of the gradient fields. In response thereof, the pacemaker switches into the electrical circuit of the pacing/sense and/or ground leads a charging source which is used to charge the implanted heart pacemaker pulse generator canister 164, leads, and/or electrodes to an electrical potential opposite to that which would be induced by the gradient fields. In this way, the induced voltages caused by the gradient fields are cancelled out or reduced to a safe level, by the application of this voltage source.

In a preferred embodiment of the present invention, the charging/voltage source receives its power from inductively coupling to the MRI system's radio-frequency field. The oscillating radio-frequency field supplies power to charge special capacitors in the implanted heart pacemaker pulse generator canister 164. It is noted that other external power sources can be used to power the charging/voltage source in the implanted heart pacemaker pulse generator canister 164.

Figure 4:
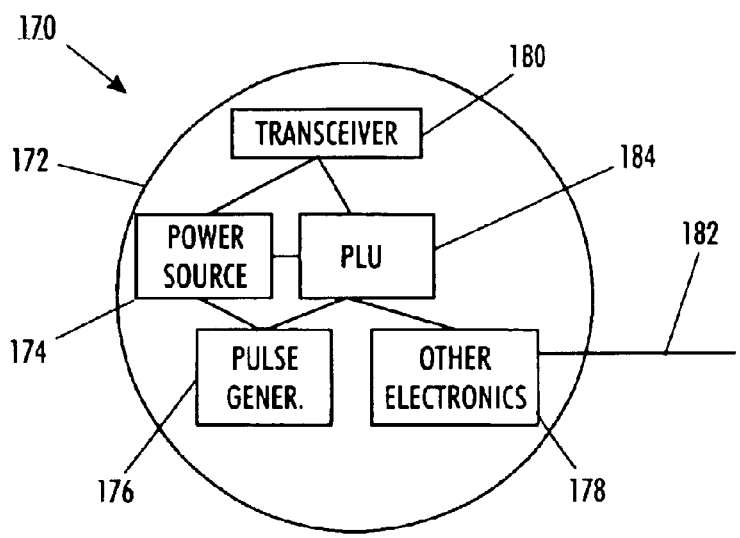
FIG. 4 illustrates an embodiment of a pacemaker canister according to the concepts of the present invention.

FIG. 4 is a diagram of an assembly 170 for the pacemaker generator components comprising the canister housing 172, a programmable logic unit (PLU) 184, a power source 174, and a pulse generator 176. Additionally, means for communicating with an external sensor/transceiver is provided by transceiver 180. Other electronic components 178; e.g., signal filters, signal processors, lead connectors, etc. are also located in the canister 172. The pacing leads 182 pass through the canister 172 and connect to the internal electronics 178. During an NRI examination, the signals transmitted and received by the transceiver 180 may be used to synchronize the MRI system's scanning sequences with the delivery of the pacing signals.

Figure 5:
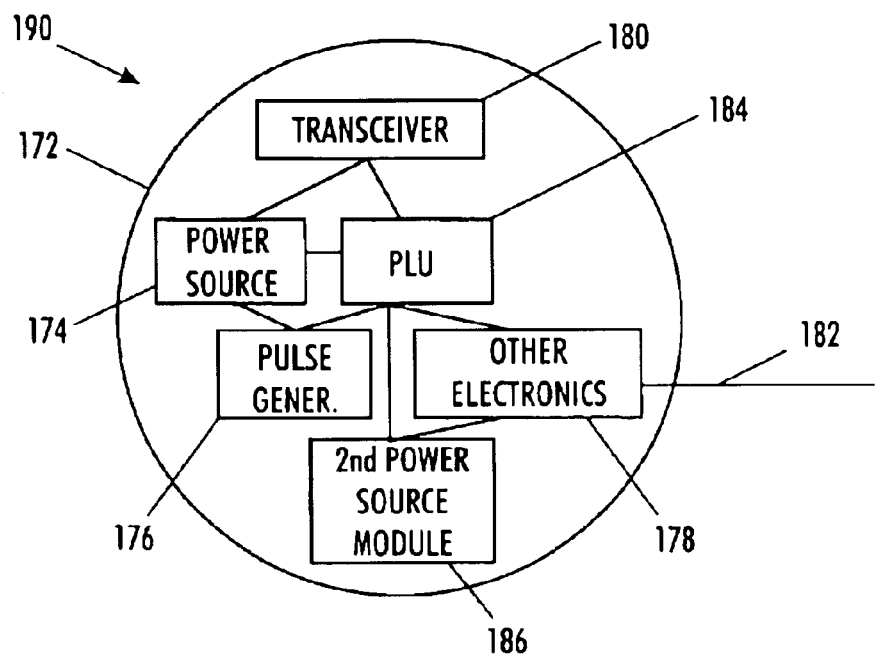
FIG. 5 illustrates another embodiment of a pacemaker canister according to the concepts of the present invention.

In another embodiment, as depicted in FIG. 5, the pacing generator assembly 190 further includes a second power module 186 which may be an inductive coil and/or capacitor bank, suitable for capturing and storing power from the MRI system's transmitted radio-frequency signal.

In one embodiment, the power stored in the power module 186 is used to develop an electrical potential in the leads 182 that is opposed to that which is induced by the application of the MRI system's gradient fields.

In another embodiment, the power stored in the power module 186 is used to operate various switches in the electronics module 178 which may switch in or out various power serge protection circuits in-line and/or signal filters to the leads 182.

In a further embodiment, and referring to FIG. 5, the module 186 may be used to electrically charge the pacemaker canister 172, which is made of a conductive material, in synchronization with the application of the MRI system's gradient fields so that the electrical potential difference between the pacing electrodes and the pacemaker canister 172 is reduced. That is, the sum of the induced voltage difference due to the application of the gradient fields plus the voltage difference due to the application of the electrical charge stored in the power module 186 results is a net voltage significantly below any threshold level, above which a problem may develop.

Figure 6:
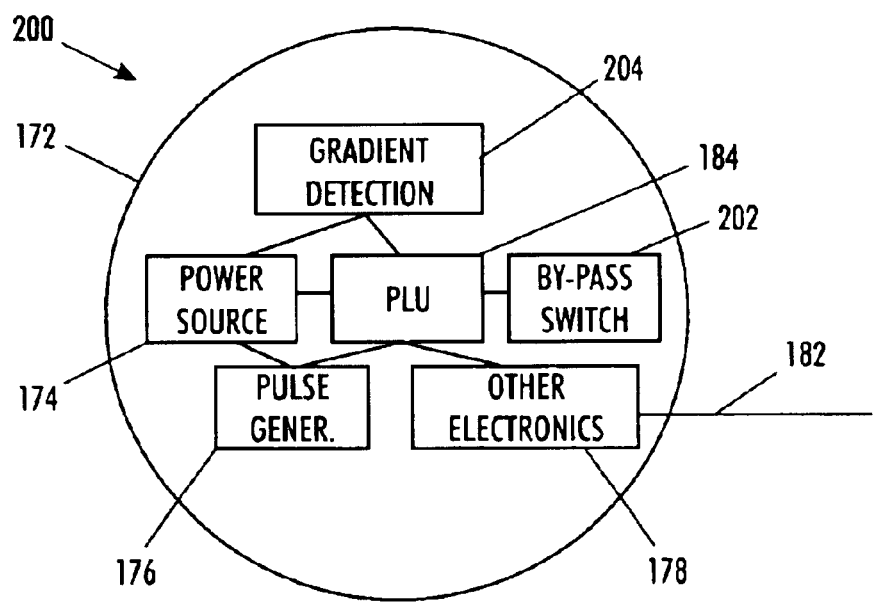
FIG. 6 illustrates a further embodiment of a pacemaker canister according to the concepts of the present invention.

FIG. 6 depicts another assembly 200, which includes the basic components of FIG. 5 less the transceiver 180, a gradient field detector 204, and a by-pass switch component 202. By detecting the gradient signal in the pacemaker canister 172 with gradient field detector 204, the pacemaker can switch filters and/or other electronics 178 in or out of the circuit.

In one embodiment, when no gradient fields are detected, the switch 202 is closed to by-pass the electronics component 178, which may be a combination of low-pass, high-pass, notch filters, diodes, and/or other electronics. In this mode (switched closed), the pacing pulse (and sensing signals) by-pass the filters components 178. When gradient field detector 204 detects the gradient signals, the switch 202 is opened and any gradient fields induced signals in the leads 182 are blocked or significantly reduced by the filters components 178. In the open mode, the pacing and sensing signals pass through the filters component 178 as well.

The gradient detector 204 may communicate the sensing of the gradient field to other components in the pacemaker via its connection to the PLU 184 so that the pacing signal can be modified, if necessary, to compensate for any distortion it may suffer by now going through the filters component 178. Additionally, the sensing signal, now also passing through the filter components 178 may be distorted. This may be compensated for by including signal recovery/reconstruction logic into the PLU or into a separate signal-processing component.

Referring back to FIG. 1, by increasing the impedance of the leads 104, the voltage across the tissue gap from the electrodes 112 and the pacemaker canister 102 can be reduced. Inserting a resistor or using a higher resistive wire for the pacemaker leads 104 will reduce the current induced in the current loop, which includes the virtual loop portion across the (heart 112) tissue to the pacemaker generator canister 102.

By using various inductors in-line with the various leads 104, it is possible to make the leads 104 have a high impedance for the low frequency MRI gradient fields frequency and a low impedance for the MRI system's radio-frequency frequency. Alternatively, different impedances (inductors/resistors/capacitors) may be switched in-line or out of the leads' circuitry depending on the timing and application of the gradient and/or radio-frequency fields.

In another embodiment, not shown, the pacemakers' electronics can be augmented to include one or more digital signal processors. By converting the sensing signal into a digital signal, the digital signal processor (DSP) can reconstruct the sensing signal after it has passed through filters and has been distorted by the filtering or other elements that may have been added to the lead circuit. The DSP may also be used to reject any signals that do not have a correct cardiac signature, thus rejecting any signals caused by the switched gradient fields, which is a non-cardiac signal.

In another embodiment of the present invention, a pacemaker lead or other medical device, having a long conductive lead and functioning in an MRI environment, may be configured, according to the concepts of the present invention, to include additional loops to cancel the induced voltage effects in the leads of the original current loop formed by the leads.

Figure 7:
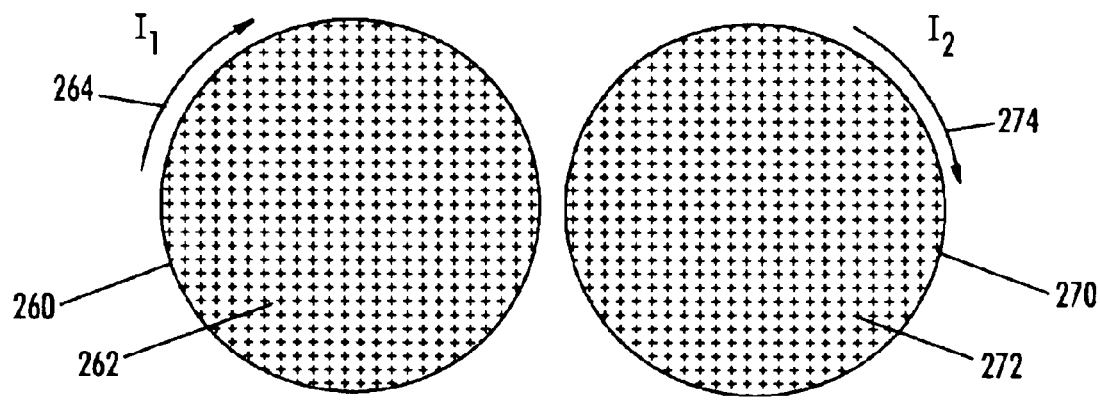
FIG. 7 is an illustration of inductive currents in conductor loops.

In FIG. 7, two conductive loops 260 and 270 having the same amount of area and in the same plane, positioned in a changing magnetic field 262 and 272, develop currents 264 and 274. In FIG. 7, both induced currents $I_1$ and $I_2$ travel in the same direction (clockwise direction shown) at all times as the magnetic field 262 and 272 oscillate.

Figure 8:
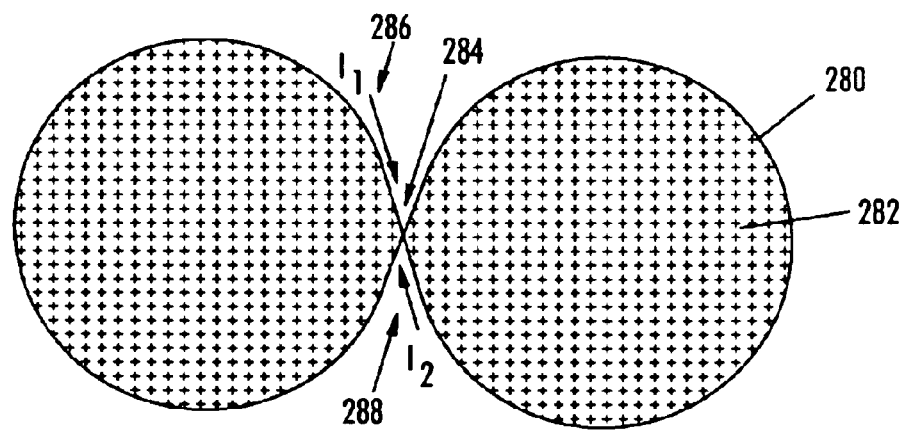
FIG. 8 is an illustration of canceling inductive currents in conductor loops according to the concepts of the present invention.

FIG. 8 shows that by connecting the two conductive loops 260 and 270 of FIG. 7 to form a single conductor 280, the currents induced in each lobe can be made to cancel each other out. The two loops are connected so that a single conductor is formed which crosses over itself at 284. In this case, as shown in FIG. 8, the two currents 286 and 288 cancel each other out resulting in net current of zero magnitude around the conductor 280. This type of configuration of conductors in a changing magnetic field may be used to cancel induced currents in the conductors.

Figure 9:
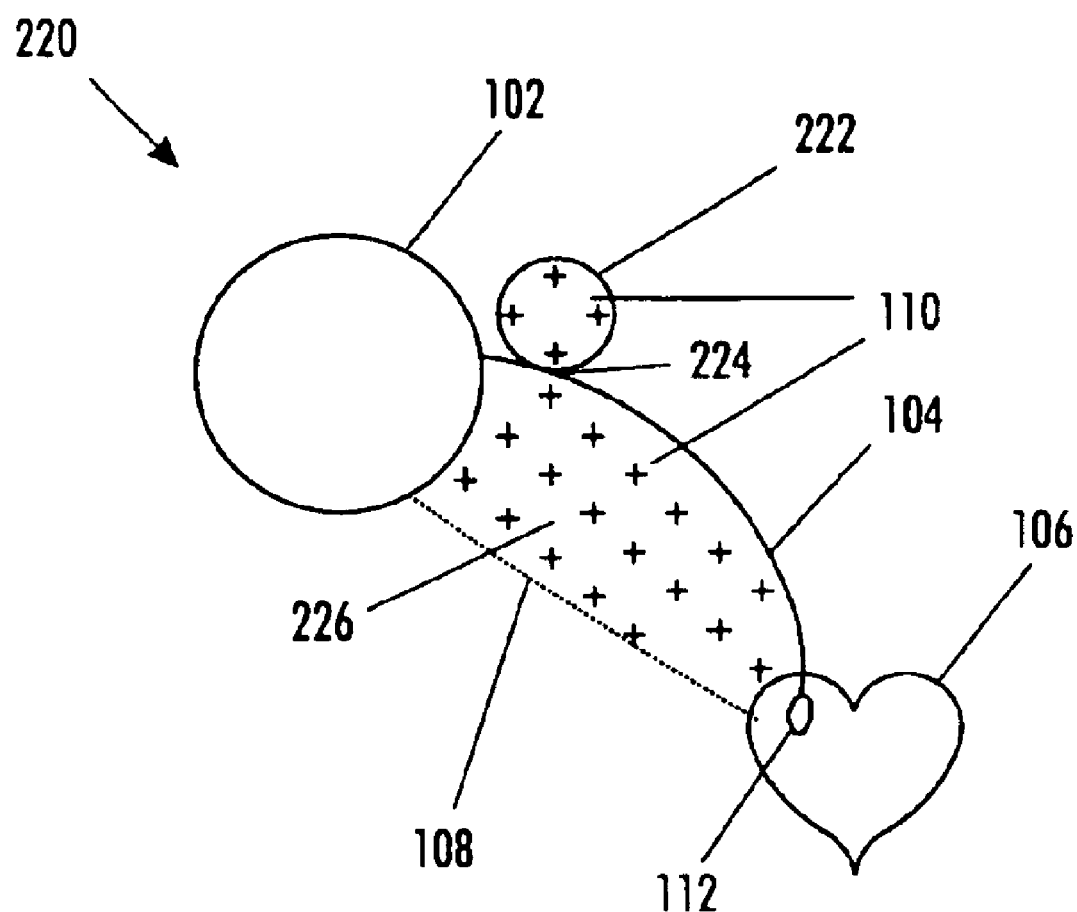
FIG. 9 is a schematic of an embodiment of a pacemaker lead utilizing inductive loops according to the concepts of the present invention.

FIG. 9 depicts an implanted pacemaker system 220 comprising a pacing generator canister 102, conductive leads 104, and electrodes 112 positioned in the heart 106. Additional loops 222 are added to the overall configuration of the lead 104 in the body with one or more crossings 224. In accordance with the concepts of the present invention, the plane of the loop 222 is in the same plane as defined by the rest of the lead geometry.

The same oscillating magnetic field 110 passes through loop 222 and the loop defined by generator canister 102, conductive leads 104, electrodes 112, and conductive path 108 through the body from the heart 106 to the generator canister 102. It is noted that the total area enclosed by the loops can be adjusted by adding or removing loops 222 or by changing the area enclosed by the loops (singly or collectively).

In one embodiment, the total area of the loop 222 is the same as the loop area 226. In another embodiment, the total area of the loop 222 is different from loop area 226. In another embodiment, the plane of loop 222 is different from the plane of loop area 226. In yet another embodiment, loop 222 and/or loop area 226 do not define a single plane but are curved in three different spatial directions. In yet another embodiment, loop 222 consists of at least three loops in three orthogonal planes.

Figure 10:
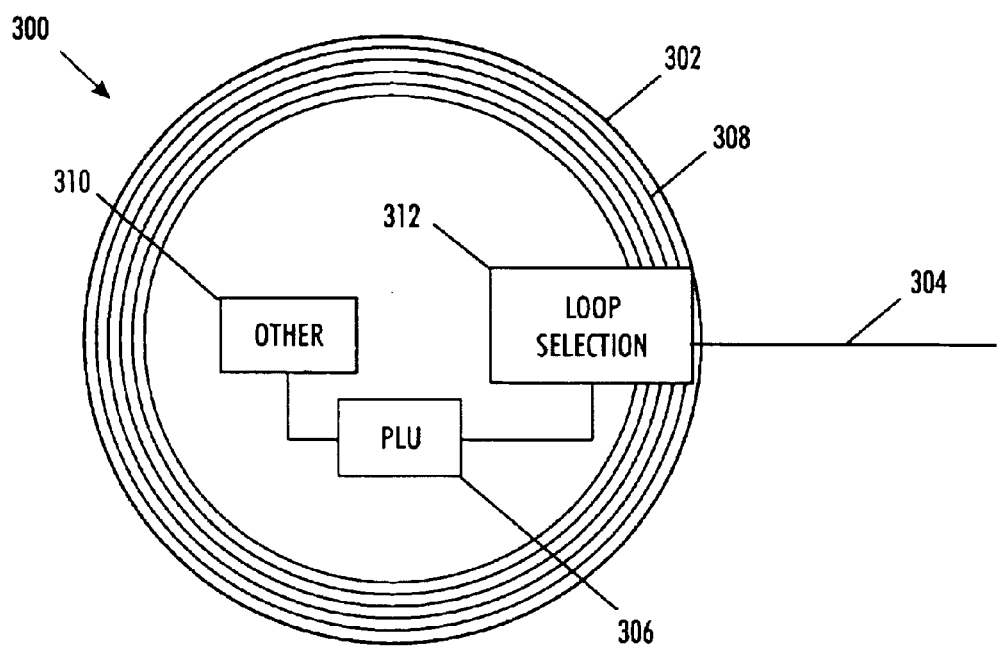
FIG. 10 is a schematic of an embodiment of inductive loops in a pacemaker canister according to the concepts of the present invention.
Figure 11:
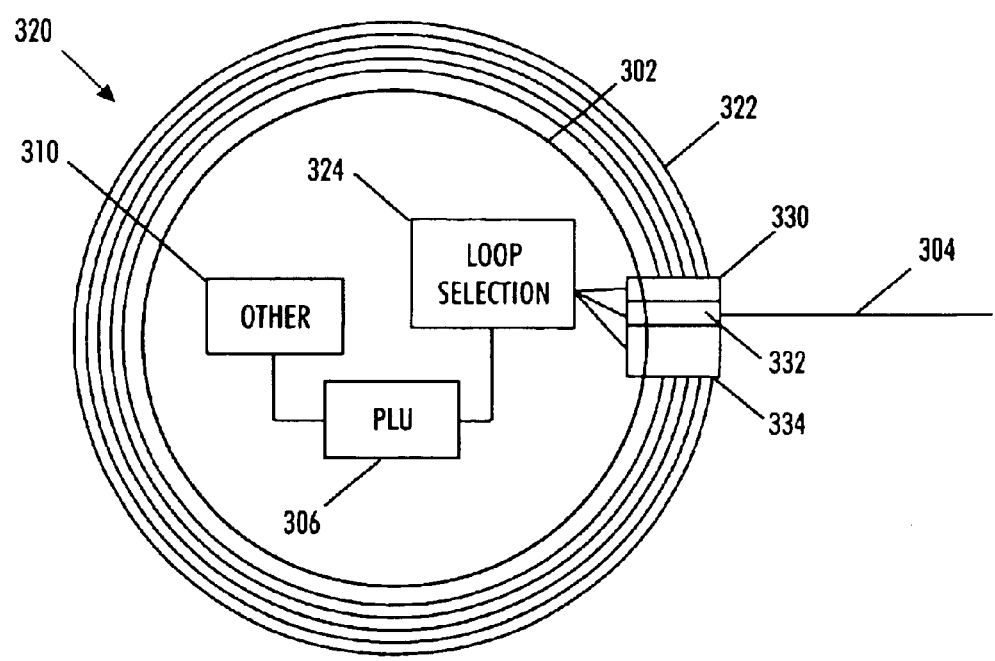
FIG. 11 is a schematic of an embodiment of inductive loops around a pacemaker canister according to the concepts of the present invention.

In a further embodiment, as illustrated in FIG. 11 and will be discussed in more detail below, the new additional loops 222 can be positioned in such a way as to encircle the pacemaker's generator canister 102. In another embodiment, as illustrated in FIG. 10 and will be discussed in more detail below, the additional loops 222 may be positioned inside the pacemaker's generator canister 102.

Referring back to FIG. 9, a fastener (not shown) can be used at the loop cross over point 224 to allow for adjustment of the loop's enclosed area and/or orientation and, once adjusted, to lock in the loop's adjustments. This same fastener can also be used to adjust a plurality of loops.

In a further embodiment of FIG. 9, pacemaker's generator canister 102 may include an orientation subsystem for automatically changing a spatial orientation of the coil to modify the strength of the MRI switched gradient field induced current. In this embodiment, the orientation subsystem may sense the magnitude of the MRI switched gradient field induced current (voltage) and spatially tune the orientation of the coils so as to produce more current to oppose the MRI switched gradient field induced current or less current to oppose the MRI switched gradient field induced current based upon the sensed magnitude of the MRI switched gradient field induced current (voltage).

In other words, if greater current is needed to oppose the MRI switched gradient field induced current, the orientation subsystem would spatially move or adjust one or more coils such that their surface planes become more perpendicular to the MRI gradient field lines, thereby inducing a greater magnitude of current to oppose the MRI switched gradient field induced current. On the other hand, if less current is needed to oppose the MRI switched gradient field induced current, the orientation subsystem would spatially move or adjust one or more coils such that their surface planes become less perpendicular and more parallel to the MRI gradient field lines, thereby inducing a lesser magnitude of current to oppose the MRI switched gradient field induced current.

In another aspect of the present invention, a selection mechanism can be included in the pacemaker system. This selection mechanism is used to adjust the number of loops to include in the circuit.

For example, if the loops are located within the pacemaker canister, the selection mechanism can be used to manually select how many loops to include in the lead circuit depending on where the pacemaker can is placed in the body and the length of the lead. Alternatively, the selection mechanism may be used to automatically select how many loops to include in the lead circuit depending on where the pacemaker can is placed in the body and the length of the lead. In this alternative embodiment, the present invention monitors the voltages on the pacemaker's lead(s) and selects a different number of loops to connect to the lead(s) to cancel any induced voltages. Lastly, the selection mechanism may be externally programmed and transmitted to the pacemaker's PLU that then monitors and adjusts the number of loops in the lead circuit.

FIG. 10 is a schematic of a pacemaker system 300 that includes a pacemaker canister 302 and the pacemaker's leads 304. The pacemaker's canister 302 contains a programmable logic unit (PLU) 306, and other electronics 310, e.g. a pulse generator, power supply, etc. The system 300 further includes conductive loops 308 positioned within the pacemaker canister 302.

The conductive loops are connected to a loop selection component 312 that provides means for selectively adjusting the number of loops to be included in the leads' circuit 304. The leads 304 are also connected to the loop selection component 312 so that the leads 304 can be electrically connected to the loops 308.

The loop selection component 312 connects the loops 308 to the leads' circuit 304 in such a way that any induced voltages in the loops 308 caused by changing magnetic fields in the environment, e.g. an MRI environment, will cancel out or significantly reduce in magnitude any induced voltage along the leads 304 that have also been caused by the environment's changing magnetic fields.

In one embodiment, the loop selection component 312 is adjusted manually by screws, connection pins, and/or other means.

In another embodiment, the loop selection component 312 is controlled by the PLU 306. The PLU 306 may include means for receiving loop selection instructions from an external transmitter or may include sensors that measure environmental variables, e.g. changing magnetic fields in an MRI environment. From this information, the PLU 306 dynamically adjusts the loop selection component's 312 adjustable parameters so as to change which loops are included in the leads' circuitry 304. It is noted that the loops 308 need not be all in the same plane.

In a further embodiment of FIG. 10, pacemaker's generator canister 302 may include an orientation subsystem for automatically changing a spatial orientation of the coil to modify the strength of the MRI switched gradient field induced current. In this embodiment, the orientation subsystem may sense the magnitude of the MRI switched gradient field induced current (voltage) and spatially tune the orientation of the coils so as to produce more current to oppose the MRI switched gradient field induced current or less current to oppose the MRI switched gradient field induced current based upon the sensed magnitude of the MRI switched gradient field induced current (voltage).

In other words, if greater current is needed to oppose the MRI switched gradient field induced current, the orientation subsystem would spatially move or adjust one or more coils such that their surface planes become more perpendicular to the MRI gradient field lines, thereby inducing a greater magnitude of current to oppose the MRI switched gradient field induced current. On the other hand, if less current is needed to oppose the MRI switched gradient field induced current, the orientation subsystem would spatially move or adjust one or more coils such that their surface planes become less perpendicular and more parallel to the MRI gradient field lines, thereby inducing a lesser magnitude of current to oppose the MRI switched gradient field induced current.

FIG. 11 is a schematic of another pacemaker system 320. Pacemaker system 320 includes conductive loops 322 positioned externally to a pacemaker canister 302. In this embodiment, the loops 332 are connected to an input port connection 330 and to an output port connection 334 which are electrically connected to the loop selection component 324 located inside the pacemaker canister 302. Additionally, the pacemaker leads 304 are connected to an electrical connector 332 that is electrically connected to the loop selection component 324. It is noted that the conductive loops 322 need not be all in the same plane.

In a further embodiment of FIG. 11, pacemaker system 320 may include an orientation subsystem for automatically changing a spatial orientation of the coil to modify the strength of the MRI switched gradient field induced current. In this embodiment, the orientation subsystem may sense the magnitude of the MRI switched gradient field induced current (voltage) and spatially tune the orientation of the coils so as to produce more current to oppose the MRI switched gradient field induced current or less current to oppose the MRI switched gradient field induced current based upon the sensed magnitude of the MRI switched gradient field induced current (voltage).

In other words, if greater current is needed to oppose the MRI switched gradient field induced current, the orientation subsystem would spatially move or adjust one or more coils such that their surface planes become more perpendicular to the MRI gradient field lines, thereby inducing a greater magnitude of current to oppose the MRI switched gradient field induced current. On the other hand, if less current is needed to oppose the MRI switched gradient field induced current, the orientation subsystem would spatially move or adjust one or more coils such that their surface planes become less perpendicular and more parallel to the MRI gradient field lines, thereby inducing a lesser magnitude of current to oppose the MRI switched gradient field induced current.

Figure 12:
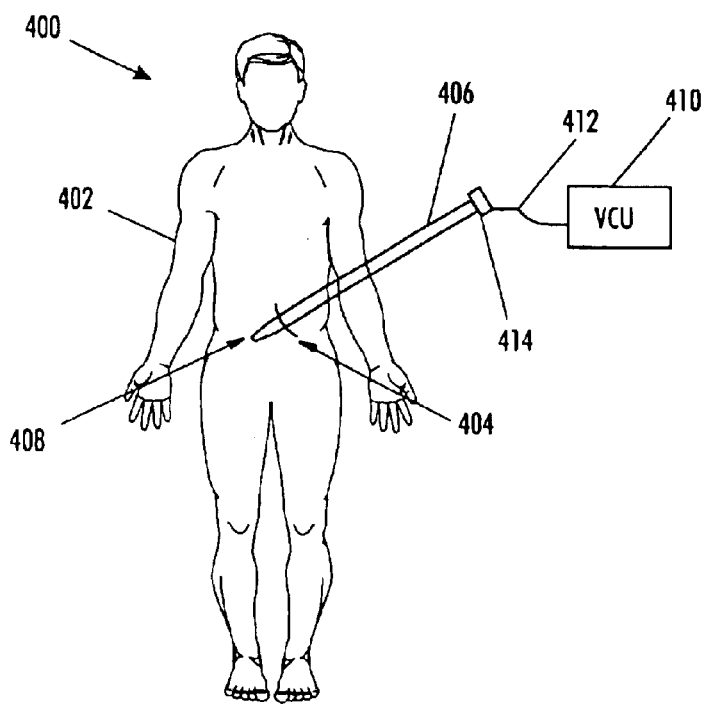
FIG. 12 illustrates of an embodiment of a medical device with an external voltage cancellation unit according to the concepts of the present invention.

FIG. 12 depicts a medical procedure in which a catheter 406 or other medical device, e.g. a guidewire, which is comprised of conductive leads or other conductive components, may be partially inserted into a body 402 and partially external to the body. In an MRI environment, such conductive medical devices 406 can develop problems like heating, induced voltages, etc. caused by the changing magnetic fields of the MRI system. To compensate for induced currents and/or induced voltages in such devices 406, a voltage compensation unit (VCU) 410 is electrically connected to the medical device 406 via conductive leads 412 and electrical connectors 414, externally to the patient's body 402.

The medical device 406 is constructed with additional electrical connectors 414 to allow for easy attachment of the VCU device 410. The VCU device 410 is connected to a power supply or may have a built in power supply, e.g. batteries. The VCU device 410 has sensors built into it, which monitor the voltages of the conductive components in the medical device 406, and delivers opposing voltages to the medical device 406 to cancel out or significantly reduce any induced voltages caused by the changing magnetic fields in an MRI (or other) environment.

Additionally or alternatively, the VCU device 410 has sensors to detect the changing magnetic fields of the MRI system and can synchronize the application of the canceling voltage with the MRI System's changing fields.

Figure 13:
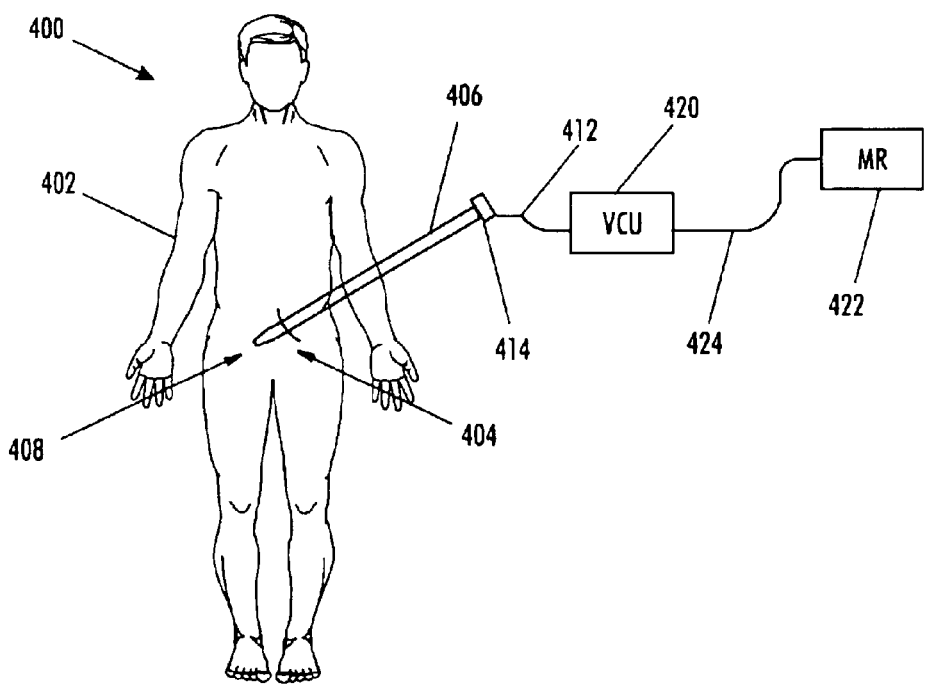
FIG. 13 illustrates of another embodiment of a medical device with an external voltage cancellation unit according to the concepts of the present invention.

In another embodiment depicted in FIG. 13, the VCU device 420 is connected to the MRI system 422 via communication means 424 so that the start and end of the application of the MRI system's 422 fields may be communicated to the VCU device 420. Other information that may be required (field strengths to be applied, MRI scan sequence, etc.) may also be communicated to the VCU device 420. The communication means 424 may be electrical wires/coaxial/shielded/other, optical fiber, or a radio-frequency transmitter/receiver, or some sonic means of communication.

The conductive lead of a heart pacemaker is a filer winding. The filer winding may consist of two or more conductive stands coiled together in a spring-like configuration. The current (pulses, signals) then flows over the surface and through the contact points between one loop and the adjacent loop of the winding, rather than following the windings of the individual conductive strands. This occurs because there is no significant insulating material or surface coating between the contact points of the windings.

In accordance with the present invention, to reduce the alternating, induced current flowing, caused by a magnetic resonance system's changing magnetic fields, through the, for example, pacemaker's winding leads, the inductance value of the pacemaker's lead may be changed to increase the overall impedance of the pacemaker's lead.

Thus in one embodiment, a suitable radio-frequency choke is inserted inline with the pacemaker's lead, prefer- able near the distal tip. For example, referring back to FIG. 2, and to the embodiment therein, electronic component 146 and/or 144 may comprise a radio-frequency choke. In a preferred embodiment, the radio-frequency choke has an inductance value of about 10 microHenries. In another embodiment, the inductance value is about 2 microHenries.

The specific value of inductance to introduce into the, for example, pacemaker's lead depends in part on the frequency of the induced signal from the MRI system's imaging sequence that is to be blocked or significantly reduced.

Figure 14:
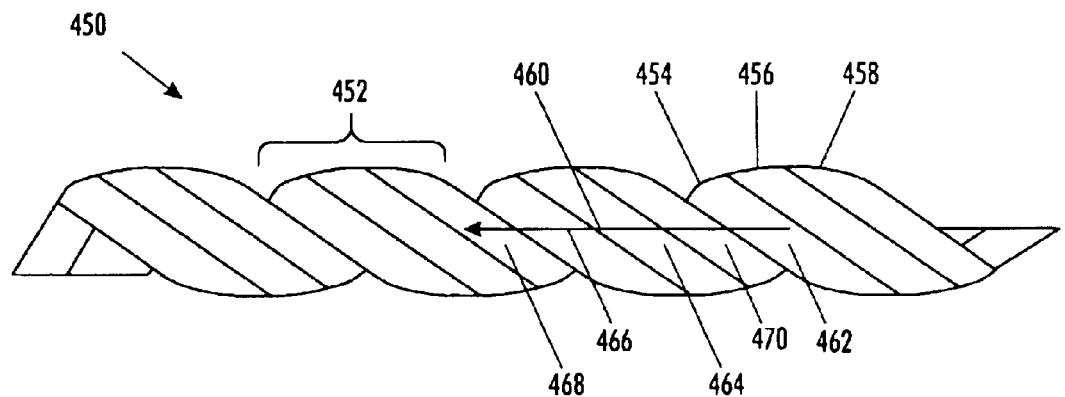
FIG. 14 illustrates a portion of coiled leads used in a medial device according to the concepts of the present invention.

FIG. 14 shows a portion of a coiled multi-filer lead 450. As illustrated in FIG. 14, lead 450 includes a plurality of coil loops 452; each coil loop 452 consists of three conductive strands 454, 456, and 458. A current 460 through the lead 450 can cross contact points 464, 466, and 462 between the strands as well as the coil contact points 468 and 470. Thus, the current 460 does not follow the coiling of the lead's conductive strands 454, 456, and 458.

Figure 15:
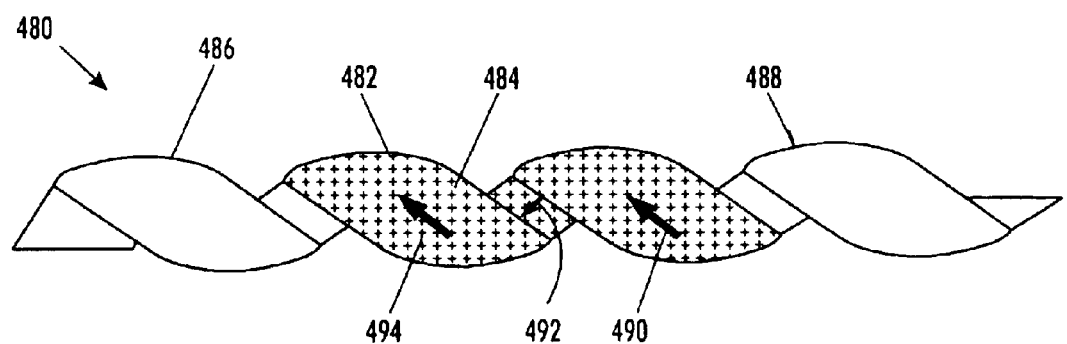
FIG. 15 illustrates another embodiment of a portion of coiled leads used in a medial device according to the concepts of the present invention.

FIG. 15 shows a portion of a coiled lead assembly 480 including a region 482 that has an insulating coating 484 applied to its surface. The coiled lead assembly 480 is depicted in an elongated position in which adjacent coil windings are not in contact with one another. It is to be understood that the normal, relaxed position of the lead assembly 480 has all adjacent coiled windings in contact.

With the addition of an insulated coating 484 over the winding region 482, the current 490, 492, and 494 is now forced to substantially follow the curvature of the coiled winding 482, thus forming an inductive coil inline with the conductive lead regions 486 and 488 which do not have an insulated coating. The inductive value of the created inductor can be adjusted by adjusting the length of the region to which the insulative coating 484 is applied.

It is noted that the coating 484 may be a partially resistive material. In such an example, the inductance is then adjusted by adjusting the resistive properties of the material 484.

Figure 16:
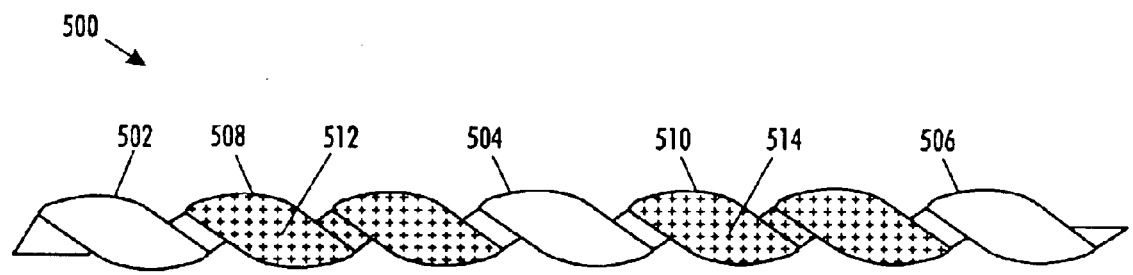
FIG. 16 illustrates a further embodiment of a portion of coiled leads used in a medial device according to the concepts of the present invention.

FIG. 16 is a schematic of a coiled lead assembly 500 comprised of uninsulated regions 502, 504, and 506, and coated insulated regions 508 and 510 with coatings 512, and 514, respectively. Through the application of the coating, the current is forced to substantially follow the curvature of the coiled windings, thus forming an inductive coil inline with the conductive lead regions that do not have a coating applied thereto. The inductive value of the created inductor can be adjusted by adjusting the length of the region to which the insulative coatings 512 and 514 are applied. In one embodiment, coatings 512 and 514 are the same coatings. In another embodiment, the coatings 512 and 514 are different materials.

It is noted that coatings 512 and 514 may be the same coating material but having differing properties, e.g., the thickness of the coatings, or the length of the coated region 508 and 510. It is further noted that the two-coated regions 508 and 510 may have different inductive values. It is also noted that more than two different regions along the length of the lead assembly can be coated.

Figure 17:
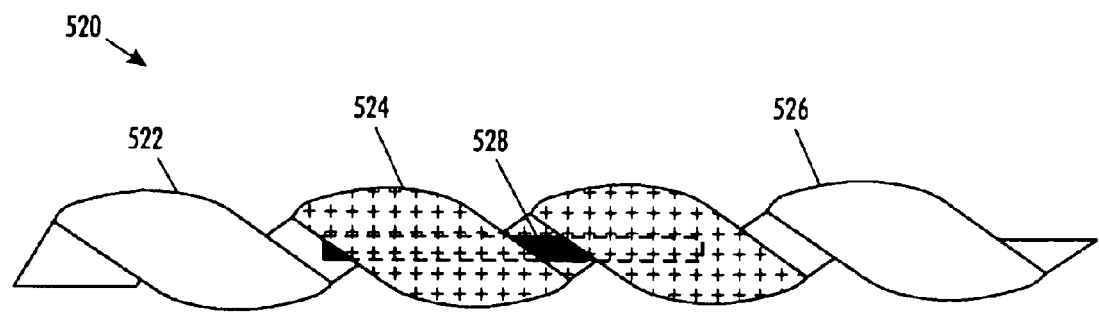
FIG. 17 illustrates another embodiment of a portion of coiled leads used in a medial device according to the concepts of the present invention.

FIG. 17 is a schematic of a portion of a coiled lead assembly 520 including at least one region 524 with a coating applied thereto. Through the application of the coating, the current is forced to substantially follow the curvature of the coiled windings, thus forming an inductive coil inline with the conductive lead regions 522 and 526 that do not have a coating applied thereto. The inductive value of the created inductor can be adjusted by adjusting the length of the region to which the insulative coating 524 is applied. Additionally, through the coated region 524 is positioned a rod 528 which also changes the inductive value of the coated region 524. It is noted that the rod 528 may be of ferrite material. It is further noted that multiple rods can be inserted into multiple coated regions along the length of the coiled lead.

It is noted that multiple coatings can be applied to the same coated region of the coiled lead wherein the multiple coating layers may be comprised of different materials. It is further noted that one or more layers of the multiple layers of coatings may comprise ferrite material.

In another embodiment of the present invention, the heating and/or induced voltages on catheters or guide wires is controlled or substantially eliminated by introducing or creating detuned characteristic impedance at a proximal ends (ends that are not within the body) of the catheters or guide wires. This introduction or creation of detuned characteristic impedance will be discussed in more detail with respect to FIGS. 18–21.

As noted above, during MRI procedures, catheters and guide wires (wire lines), with or without grounded shielding, are used to measure physiological signals. In such instances, two-wire catheters or guide wires having a grounded shield have one conductor that carries the actual measured signal and the other wire is grounded. In terms of characteristic impedance, the two-wire catheters or guide wires having a grounded shield are unbalanced. In contrast, a single wire catheter or guide wire has characteristic impedance that is balanced.

According to the concepts of the present invention, the characteristic impedance of the catheters and guide wires, used during MRI procedures, should be unbalanced at the proximal end, under all conditions, to reduce or eliminate heating and induced voltages. To realize this reduction or elimination of heating and induced voltages at the proximal end of the catheters and guide wires, used during MRI procedures, by creating an unbalanced characteristic impedance, the present invention proposes providing a Balun along the catheter and/or guide wire or at the proximal end of the catheter and/or guide wire.

Using a Balun to maintain unbalanced characteristic impedance, the reactance at the distal end of the catheter and/or guide wire approaches infinity. Thus, even when there is some potential on the wire, the unbalanced characteristic impedance has approximately four times the ground loop looses of a balanced line, thereby substantially avoiding any incident of thermal injury. An example of such an arrangement is illustrated in FIG. 18.

Figure 18:
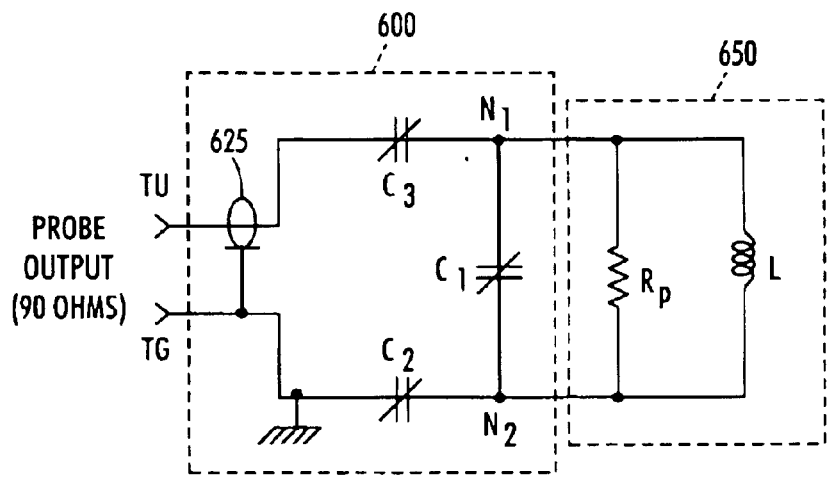
FIG. 18 illustrates a circuit diagram representing a guide wire with an unbalancing impedance circuit according to the concepts of the present invention.

As illustrated in FIG. 18, a guide wire or catheter 650 has characteristic impedance due to its intrinsic resistance from intrinsic resistor capacitors $R_P$ and its intrinsic inductance from intrinsic inductor L. To create the unbalanced characteristic impedance at the proximal end of the guide wire or catheter 650, a Balun 600 is placed along the guide wire or catheter 650. In other words, the Balun 600 is in vitro.

The Balun 600 includes a variable capacitor $C_1$ connected in parallel with the guide wire or catheter 650 and two variable capacitors $C_2$ and $C_3$ connected in series with the guide wire or catheter 650. It is noted that one end of the variable capacitor $C_2$ is connected to the shield 625 and ground or a known voltage. The capacitance of the variable capacitors $C_1$, $C_2$, and $C_3$ are adjusted to create the unbalanced characteristic impedance.

More specifically, the variable capacitors $C_1$, $C_2$, and $C_3$ may be used for both matching and providing a certain amount of balancing for the guide wire or catheter 650 characteristic impedance. In this example, the variable capacitors $C_1$, $C_2$, and $C_3$ lift the voltage on the guide wire or catheter 650 from ground. The larger the reactance of the variable capacitors $C_1$, $C_2$, and $C_3$, the more symmetric and balanced the circuit of the guide wire or catheter 650 becomes. Conversely, according to the concepts of the present invention, if the reactive capacitance of the Balun 600 is detuned (made less resonant), the circuit of the guide wire or catheter 650 becomes asymmetric and unbalanced, breaking down, to reduce the chances of thermal injury at the distal end of the guide wire or catheter 650 due to heating from induced voltages.

Figure 19:
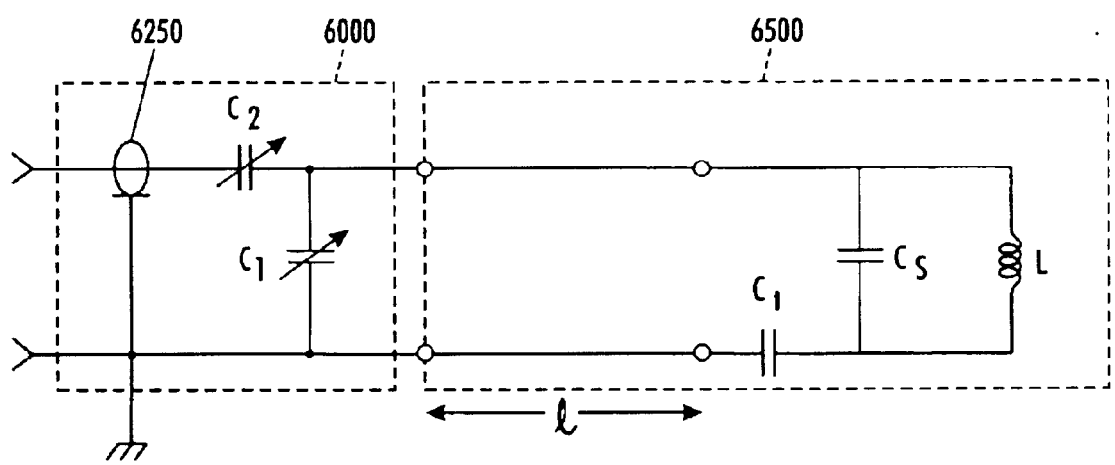
FIG. 19 illustrates another embodiment of a circuit diagram representing a guide wire with an unbalancing impedance circuit according to the concepts of the present invention.

FIG. 19 illustrates another embodiment of the present invention wherein a guide wire or catheter 6500 has characteristic impedance due to its intrinsic capacitance from intrinsic capacitors $C_p$, and $C_s$ and its intrinsic inductance from intrinsic inductor L. To create the unbalanced characteristic impedance at the proximal end of the guide wire or catheter 6500, a Balun 6000 is connected across the proximal end of the guide wire or catheter 6500. In other words, the Balun 6000 is outside the body at the proximal end of the guide wire or catheter 650. By having the Balun 6000 outside the body, the varying of the reactance of the guide wire or catheter 6500 can be readily and manually controlled.

The Balun 6000 includes a variable capacitor $C_1$ connected in parallel with the guide wire or catheter 6500 and a variable capacitor $C_2$ connected in series with the guide wire or catheter 6500. It is noted that one end of the variable capacitor $C_1$ is connected to the shield 6250 and ground or a known voltage. The capacitance of the variable capacitors $C_1$ and $C_2$ are adjusted to create the unbalanced characteristic impedance.

More specifically, the variable capacitors $C_1$, and $C_2$ may be used for both matching and providing a certain amount of balancing for the guide wire or catheter 6500 characteristic impedance. In this example, the variable capacitors $C_1$, $C_2$, and $C_3$ lift the voltage on the guide wire or catheter 6500 from ground. The larger the reactance of the variable capacitors $C_1$ and $C_2$, the more symmetric and balanced the circuit of the guide wire or catheter 6500 becomes. Conversely, according to the concepts of the present invention, if the reactive capacitance of the Balun 6000 is detuned (made less resonant), the circuit of the guide wire or catheter 6500 becomes asymmetric and unbalanced, breaking down, to reduce the chances of thermal injury at the distal end of the guide wire or catheter 6500 due to heating from induced voltages.

Figure 20:
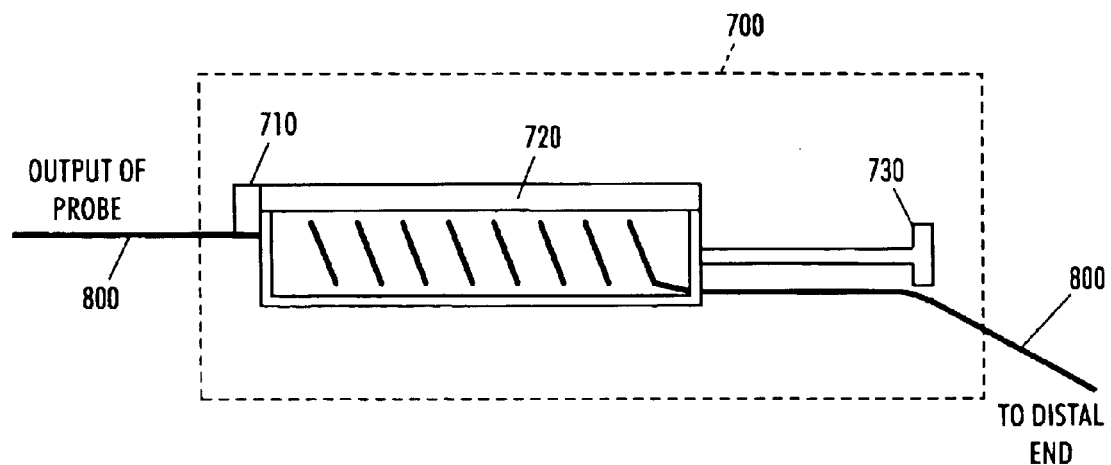
FIG. 20 illustrates a balun used in conjunction with a guide wire according to the concepts of the present invention.

FIG. 20 illustrates a further embodiment of the present invention wherein a guide wire or catheter 800 is connected to a Balun 700. The Balun 700 includes a variable capacitor 710, a copper foil 720, and a non-conductive tuning bolt 730. The Balun 700 is further connected to the output of the probe 800

The Balun 700 adjusts its characteristic impedance by increasing or decreasing the number wire coils are found within the copper foil 720. The combination of the coils and the copper foil 720 forms a variable capacitor, having it impedance determined by the change in the surface area of the coils positioned opposite of the copper foil 720. As more coils are introduced into the volume created by the copper foil 720, the capacitance of this combination increases. Moreover, as fewer coils are introduced into the volume created by the copper foil 720, the capacitance of this combination decreases. Thus, the capacitance of the Balun 700 is adjusted to create the unbalanced characteristic impedance.

Figure 21:
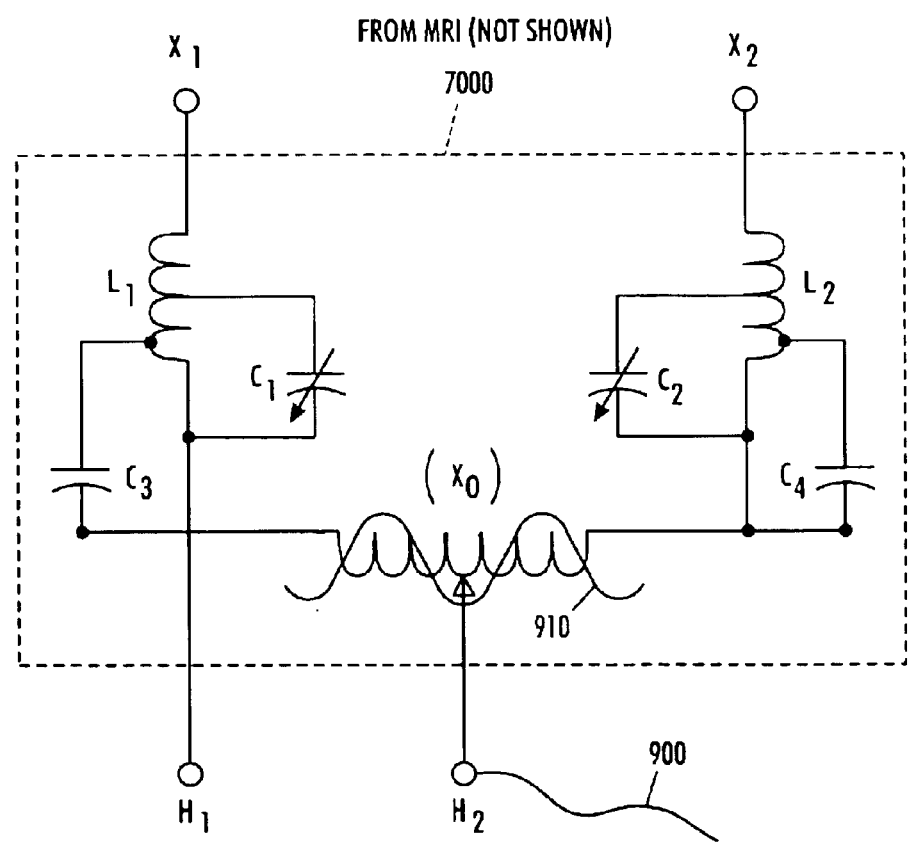
FIG. 21 is a circuit diagram representing a capacitance unbalanced balun unit according to the concepts of the present invention.

FIG. 21 illustrates another embodiment of the present invention wherein a guide wire or catheter 900 is electronically isolated by a voltage control unit to always appear as an unbalanced line to any possible magnetic field that may be applied from a magnetic resonance imager unit (not shown). As current begins to flow due to the changing magnetic fields from the magnetic resonance imaging, a tapped voltage from a voltage-controlled oscillator in the magnetic resonance imaging unit is applied across terminals X1 and X2 of the voltage control unit.

According to the concepts of the present invention, to automatically maintain an unbalanced characteristic impedance at the distal end of the guide wire or catheter 900, a capacitance unbalanced balun unit 7000, located within the voltage control unit, is connected through a variable inductor 910 to the proximal end of the guide wire or catheter 900. In other words, the voltage control unit containing the capacitance unbalanced balun unit 7000 is outside the body at the proximal end of the guide wire or catheter 900. By having the capacitance unbalanced balun unit 7000 and variable. inductor 910 outside the body, the varying of the reactance (X0) of the guide wire or catheter 900 can be readily adjusted and automatically controlled by the voltage control unit circuit's reactance to the tapped voltage from the voltage-controlled oscillator in the magnetic resonance imaging unit as it is applied across X1 and X2 for any instance of time from time zero (T0) or instantation of the magnetic resonance imaging radio-frequency pulses.

The capacitance unbalanced balun unit 7000 includes two non-magnetic trimmer capacitors C1 and C2 connected in parallel with LC circuits (L1,C3) and (L2,C4), respectively, setting up a simplified dual T network that is effectively in series with the guide wire or catheter 900. It is noted that one end of the simplified dual T network is connected to neutral H1 and the other end is connected to a continuously variable voltage H2, based on inputs to the circuit from the voltage-controlled oscillator in the magnetic resonance imaging unit at X1 and X2. The reactance (X0) of the LC circuits in the T network is automatically adjusted to create the desired unbalanced characteristic impedance.

More specifically, the T network L1, C1, C3 and L2, C2, C4 respectively, may be used for both matching and unmatching characteristic impedance of the guide wire or catheter 900 and to provide a certain amount of balancing or unbalancing for the guide wire or catheter 900 by varying the circuit's capacitive or inductive reactance (X0).

In this example, as the voltage from the voltage-controlled oscillator in the magnetic resonance imaging unit is provided to the voltage control unit (X1 X2), the two non-magnetic trimmer capacitors C1 and C2, connected in parallel with LC circuits, (L1,C3) and (L2,C4), lift the voltage on the guide wire or catheter 900 from ground to an unbalanced state with respect to the radio-frequency pulse applied by the magnetic resonance imaging unit. The reactance of the T network and its LC circuits, (L1,C3) and (L2,C4), respectively, cause the guide wire or catheter 900 to become asymmetric and unbalanced, automatically breaking down the reactance to ensure that resonance for the guide wire or catheter 900 is never present, thus reducing the chances of thermal injury at the distal end of the guide wire or catheter 900 due to heating from induced voltages.

In summary, the present invention is directed to a system for reducing the effects of MRI induced signals to a safe level having a medical device that includes a housing having electronic circuitry therein, a first lead to provide an electrical path for a stimulation signal generated by the electronic circuitry to be applied to a desired tissue region, a second lead to provide an electrical path for a sensed physiological condition of the desired tissue region to be communicated to the electronic circuitry, and a third lead to provide an electrical ground. A diode is connected to the first lead to significantly reduce MRI induced signals from traveling along the first lead to the electronic circuitry.

This embodiment of the present invention may also include a filter, connected to the second lead, to significantly reduce MRI induced signals from traveling along the second lead to the electronic circuitry; a second filter, connected to the third lead, to significantly reduce MRI induced signals from traveling along the third lead to the electronic circuitry; a sensor to sense application of switched MRI gradient fields; an electronic component, connected to the second lead, to significantly reduce MRI induced signals from traveling along the second lead to the electronic circuitry; and/or a switch, connected to the sensor and the electronic component, to operatively connect the electronic component to the second lead when the sensor senses the application of switched MRI gradient fields and to operatively disconnect the electronic component from the second lead when the sensor fails to sense the application of switched MRI gradient fields.

In this embodiment the electronic component may be a filter, impedance, an inductor, a resistor, and/or a capacitor. The electronic component may be a source that generates an electrical potential opposite to that which would be induced by the MRI switched gradient fields so as to reduce voltages induced by the MRI switched gradient fields to a safe level or a coil that generates a MRI switched gradient field induced current opposite to that which would be induced by the MRI switched gradient fields in the leads so as to reduce voltages induced by the MRI switched gradient fields to a safe level wherein the coil may be curved in three different spatial directions. The electronic component having the coil may also include an orientation subsystem for changing a spatial orientation of the coil to modify the strength of the MRI switched gradient field induced current.

The electronic component may include a plurality of coils, each coil generating a MRI switched gradient field induced current opposite to that which would be induced by the MRI switched gradient fields in the leads so as to reduce voltages induced by the MRI switched gradient fields to a safe level, and a switch connecting independently a number of the plurality of the coils, the number of connected coils corresponding to an amount of the voltage induced by the MRI switched gradient fields and a current level produced in each coil when the sensor senses the application of switched MRI gradient fields wherein the coils are curved in three different spatial directions. The electronic component may also include an orientation subsystem for changing a spatial orientation of the coils to modify the strength of the MRI switched gradient field induced currents.

The electronic component may be three orthogonally planar coils, each coil generating a MRI switched gradient field induced current opposite to that which would be induced by the MRI switched gradient fields in the leads so as to reduce voltages induced by the MRI switched gradient fields to a safe level, and a switch connecting independently a number of the coils, the number of connected coils corresponding to an amount of the voltage induced by the MRI switched gradient fields and a current level produced in each coil when the sensor senses the application of switched MRI gradient fields. The electronic component may also include an orientation subsystem for changing a spatial orientation of the coils to modify the strength of the MRI switched gradient field induced currents wherein each coil defines a distinct plane that transverses the MRI switched gradient fields.

This embodiment may also include a receiver to receive a signal from a MRI system indicating an application of switched MRI gradient fields; an electronic component, operatively connected to the second lead, to significantly reduce MRI induced signals from traveling along the second lead to the electronic circuitry; and a switch, operatively connected to the receiver and the electronic component, to operatively connect the electronic component to the second lead when the receiver receives an indication of the application of switched MRI gradient fields and to operatively disconnect the electronic component from the second lead when the receiver receives a signal indicating no application of switched MRI gradient fields. The electronic component may be a filter, impedance, an inductor, a resistor, and/or a capacitor.

The electronic component may be a source that generates an electrical potential opposite to that which would be induced by the MRI switched gradient fields so as to reduce voltages induced by the MRI switched gradient fields to a safe level or a coil that generates a MRI switched gradient field induced current opposite to that which would be induced by the MRI switched gradient fields in the leads so as to reduce voltages induced by the MRI switched gradient fields to a safe level wherein the coil may be curved in three different spatial directions. The electronic component having the coil may also include an orientation subsystem for changing a spatial orientation of the coil to modify the strength of the MRI switched gradient field induced current.

The electronic component may include a plurality of coils, each coil generating a MRI switched gradient field induced current opposite to that which would be induced by the MRI switched gradient fields in the leads so as to reduce voltages induced by the MRI switched gradient fields to a safe level, and a switch connecting independently a number of the plurality of the coils, the number of connected coils corresponding to an amount of the voltage induced by the MRI switched gradient fields and a current level produced in each coil when the sensor senses the application of switched MRI gradient fields wherein the coils are curved in three different spatial directions. The electronic component may also include an orientation subsystem for changing a spatial orientation of the coils to modify the strength of the MRI switched gradient field induced currents.

The electronic component may be three orthogonally planar coils, each coil generating a MRI switched gradient field induced current opposite to that which would be induced by the MRI switched gradient fields in the leads so as to reduce voltages induced by the MRI switched gradient fields to a safe level, and a switch connecting independently a number of the coils, the number of connected coils corresponding to an amount of the voltage induced by the MRI switched gradient fields and a current level produced in each coil when the sensor senses the application of switched MRI gradient fields. The electronic component may also include an orientation subsystem for changing a spatial orientation of the coils to modify the strength of the MRI switched gradient field induced currents wherein each coil defines a distinct plane that transverses the MRI switched gradient fields.

In another embodiment, the present invention is directed to a system for reducing the effects of MRI induced signals to a safe level. The system includes a MRI system; a medical device; and a transceiver to provide communication between the MRI system and the medical device. The medical device has a housing having electronic circuitry therein, a bi-directional lead to provide an electrical path for a stimulation signal generated by the electronic circuitry to be applied to a desired tissue region and to provide an electrical path for a sensed physiological condition of the desired tissue region to be communicated to the electronic circuitry, and a lead to provide an electrical ground. The medical device indicates to the MRI system, through the transceiver, when the stimulation signal will be applied to the desired tissue region. The MRI system, in response to the indication from the medical device of when the stimulation signal will be applied to the desired tissue region, terminates a production of MRI switched gradient fields.

This embodiment may further include a filter, connected to the bi-directional lead, to significantly reduce MRI induced signals from traveling along the bi-directional lead to the electronic circuitry; a filter, connected to the lead, to significantly reduce MRI induced signals from traveling along the lead to the electronic circuitry; a sensor to sense application of switched MRI gradient fields; an electronic component, connected to the bi-directional lead, to significantly reduce MRI induced signals from traveling along the bi-directional lead to the electronic circuitry; and/or a switch, connected to the sensor and the electronic component, to operatively connect the electronic component to the bi-directional lead when the sensor senses the application of switched MRI gradient fields and to operatively disconnect the electronic component from the bi-directional lead when the sensor fails to sense the application of switched MRI gradient fields. The electronic component may be a filter, impedance, an inductor, a resistor, and/or a capacitor.

The electronic component may be a source that generates an electrical potential opposite to that which would be induced by the MRI switched gradient fields so as to reduce voltages induced by the MRI switched gradient fields to a safe level or a coil that generates a MRI switched gradient field induced current opposite to that which would be induced by the MRI switched gradient fields in the leads so as to reduce voltages induced by the MRI switched gradient fields to a safe level wherein the coil may be curved in three different spatial directions. The electronic component having the coil may also include an orientation subsystem for changing a spatial orientation of the coil to modify the strength of the MRI switched gradient field induced current.

The electronic component may include a plurality of coils, each coil generating a MRI switched gradient field induced current opposite to that which would be induced by the MRI switched gradient fields in the leads so as to reduce voltages induced by the MRI switched gradient fields to a safe level, and a switch connecting independently a number of the plurality of the coils, the number of connected coils corresponding to an amount of the voltage induced by the MRI switched gradient fields and a current level produced in each coil when the sensor senses the application of switched MRI gradient fields wherein the coils are curved in three different spatial directions. The electronic component may also include an orientation subsystem for changing a spatial orientation of the coils to modify the strength of the MRI switched gradient field induced currents.

The electronic component may be three orthogonally planar coils, each coil generating a MRI switched gradient field induced current opposite to that which would be induced by the MRI switched gradient fields in the leads so as to reduce voltages induced by the MRI switched gradient fields to a safe level, and a switch connecting independently a number of the coils, the number of connected coils corresponding to an amount of the voltage induced by the MRI switched gradient fields and a current level produced in each coil when the sensor senses the application of switched MRI gradient fields. The electronic component may also include an orientation subsystem for changing a spatial orientation of the coils to modify the strength of the MRI switched gradient field induced currents wherein each coil defines a distinct plane that transverses the MRI switched gradient fields.

In a further embodiment, the present invention is directed to a system for reducing the effects of MRI induced signals to a safe level. The system includes a medical device wherein the medical device has a housing having electronic circuitry therein, leads to provide an electrical path for a stimulation signal generated by the electronic circuitry to be applied to a desired tissue region and to provide an electrical path for a sensed physiological condition of the desired tissue region to be communicated to the electronic circuitry, a sensor to sense application of switched MRI gradient fields, an electronic component, operatively connected to the leads, to significantly reduce MRI induced signals from traveling along the leads to the electronic circuitry, and a switch, operatively connected to the sensor and the electronic component, to operatively connect the electronic component to the leads when the sensor senses the application of switched MRI gradient fields and to operatively disconnect the electronic component from the leads when the sensor fails to sense the application of switched MRI gradient fields.

In this embodiment, the electronic component may be a source that generates an electrical potential opposite to that which would be induced by the MRI switched gradient fields so as to reduce voltages induced by the MRI switched gradient fields to a safe level or a coil that generates a MRI switched gradient field induced current opposite to that which would be induced by the MRI switched gradient fields in the leads so as to reduce voltages induced by the MRI switched gradient fields to a safe level wherein the coil may be curved in three different spatial directions. The electronic component having the coil may also include an orientation subsystem for changing a spatial orientation of the coil to modify the strength of the MRI switched gradient field induced current.

The electronic component may include a plurality of coils, each coil generating a MRI switched gradient field induced current opposite to that which would be induced by the MRI switched gradient fields in the leads so as to reduce voltages induced by the MRI switched gradient fields to a safe level, and a switch connecting independently a number of the plurality of the coils, the number of connected coils corresponding to an amount of the voltage induced by the MRI switched gradient fields and a current level produced in each coil when the sensor senses the application of switched MRI gradient fields wherein the coils are curved in three different spatial directions. The electronic component may also include an orientation subsystem for changing a spatial orientation of the coils to modify the strength of the MRI switched gradient field induced currents.

The electronic component may be three orthogonally planar coils, each coil generating a MRI switched gradient field induced current opposite to that which would be induced by the MRI switched gradient fields in the leads so as to reduce voltages induced by the MRI switched gradient fields to a safe level, and a switch connecting independently a number of the coils, the number of connected coils corresponding to an amount of the voltage induced by the MRI switched gradient fields and a current level produced in each coil when the sensor senses the application of switched MRI gradient fields. The electronic component may also include an orientation subsystem for changing a spatial orientation of the coils to modify the strength of the MRI switched gradient field induced currents wherein each coil defines a distinct plane that transverses the MRI switched gradient fields.

In a further embodiment, the present invention is directed to an electrical lead component for a medical device that reduces the effects of MRI induced signals to a safe level. The electrical lead component includes a medical device electrical lead capable of providing an electrical path to a desired tissue region and a coil that generates a MRI switched gradient field induced current opposite to that which would be induced by the MRI switched gradient fields in the medical device electrical lead so as to reduce voltages induced by the MRI switched gradient fields to a safe level. The coil may be curved in three different spatial directions.

The embodiment may further include an orientation subsystem for changing a spatial orientation of the coil to modify the strength of the MRI switched gradient field induced current.

In a further embodiment, the present invention is directed to an electrical lead component for a medical device that reduces the effects of MRI induced signals to a safe level. The electrical lead component includes a medical device electrical lead capable of providing an electrical path to a desired tissue region and a plurality of coils, each coil generating a MRI switched gradient field induced current such a combination of the MRI switched gradient field induced currents provide a combined current that is opposite to that which would be induced by the MRI switched gradient fields in the medical device electrical lead so as to reduce voltages induced by the MRI switched gradient fields to a safe level. The coil may be curved in three different spatial directions.

The embodiment may further include an orientation subsystem for changing a spatial orientation of the coil to modify the strength of the MRI switched gradient field induced current.

In a further embodiment, the present invention is directed to an electrical lead component for a medical device that reduces the effects of MRI induced signals to a safe level. The electrical lead component includes a medical device electrical lead capable of providing an electrical path to a desired tissue region and three orthogonally planar coils, each coil generating a MRI switched gradient field induced current such a combination of the MRI switched field induced currents provide a combined current that is opposite to that which would be induced by the MRI switched gradient fields in the medical device electrical lead so as to reduce voltages induced by the MRI switched gradient fields to a safe level.

In a further embodiment, the present invention is directed to an electrical lead component for a medical device that reduces the effects of MRI induced signals to a safe level. The electrical lead component includes a medical device electrical lead capable of providing an electrical path to a desired tissue region; a plurality of coils, each coil generating a MRI switched gradient field induced current; a sensor to measure a strength of voltages induced by the MRI switched gradient fields; and a switching device, operatively connected to the sensor and plurality of coils, to operatively connect a number of the plurality of coils in response to the measured strength of voltages induced by the MRI switched gradient fields such that a combination of the MRI switched gradient field induced currents produced by the number of operatively connected switches provide a combined current that is opposite to that which would be induced by the MRI switched gradient fields in the medical device electrical lead so as to reduce voltages induced by the MRI switched gradient fields to a safe level. The coils may be curved in three different spatial directions.

The embodiment may further include an orientation subsystem for changing a spatial orientation of the coil to modify the strength of the MRI switched gradient field induced current.

In a further embodiment, the present invention is directed to an electrical lead component for a medical device that reduces the effects of MRI induced signals to a safe level. The electrical lead component includes a medical device electrical lead capable of providing an electrical path to a desired tissue region; three orthogonally planar coils, each coil generating a MRI switched gradient field induced current; a sensor to measure a strength of voltages induced by the MRI switched gradient fields; and a switching device, operatively connected to the sensor and the coils, to operatively connect a number of the coils in response to the measured strength of voltages induced by the MRI switched gradient fields such that a combination of the MRI switched gradient field induced currents produced by the number of operatively connected switches provide a combined current that is opposite to that which would be induced by the MRI switched gradient fields in the medical device electrical lead so as to reduce voltages induced by the MRI switched gradient fields to a safe level.

In a further embodiment, the present invention is directed to an electrical lead component for a medical device that reduces the effects of MRI induced signals to a safe level. The electrical lead component includes a medical device electrical lead capable of providing an electrical path to a desired tissue region; a plurality of coils, each coil generating a MRI switched gradient field induced current; a transceiver to receive a signal indicating a number of coils to be connected; and a switching device, operatively connected to the transceiver and plurality of coils, to operatively connect a number of the plurality of coils in response to the received signal indicating the number of coils to be connected such that a combination of the MRI switched gradient field induced currents produced by the number of operatively connected switches provide a combined current that is opposite to that which would be induced by the MRI switched gradient fields in the medical device electrical lead so as to reduce voltages induced by the MRI switched gradient fields to a safe level. The coils may be curved in three different spatial directions.

The embodiment may further include an orientation subsystem for changing a spatial orientation of the coil to modify the strength of the MRI switched gradient field induced current.

In a further embodiment, the present invention is directed to an electrical lead component for a medical device that reduces the effects of MRI induced signals to a safe level. The electrical lead component includes a medical device electrical lead capable of providing an electrical path to a desired tissue region; three orthogonally planar coils, each coil generating a MRI switched gradient field induced current; a transceiver to receive a signal indicating a number of coils to be connected; and a switching device, operatively connected to the transceiver and the coils, to operatively connect a number of the coils in response to the received signal indicating the number of coils to be connected such that a combination of the MRI switched gradient field induced currents produced by the number of operatively connected switches provide a combined current that is opposite to that which would be induced by the MRI switched gradient fields in the medical device electrical lead so as to reduce voltages induced by the MRI switched gradient fields to a safe level.

In a further embodiment, the present invention is directed to a medical device that reduces the effects of MRI induced signals to a safe level. The medical device includes a medical device capable of providing medical treatment to a desired tissue region and a coil that generates a MRI switched gradient field induced current opposite to that which would be induced by the MRI switched gradient fields in the medical device so as to reduce voltages induced by the MRI switched gradient fields to a safe level. The coil may be curved in three different spatial directions.

The embodiment may further include an orientation subsystem for changing a spatial orientation of the coil to modify the strength of the MRI switched gradient field induced current.

In a further embodiment, the present invention is directed to a medical device that reduces the effects of MRI induced signals to a safe level. The medical device includes a medical device capable of providing medical treatment to a desired tissue region and a plurality of coils, each coil generating a MRI switched gradient field induced current such a combination of the MRI switched gradient field induced currents provide a combined current that is opposite to that which would be induced by the MRI switched gradient fields in the medical device so as to reduce voltages induced by the MRI switched gradient fields to a safe level. The coils may be curved in three different spatial directions.

The embodiment may further include an orientation subsystem for changing a spatial orientation of the coil to modify the strength of the MRI switched gradient field induced current.

In a further embodiment, the present invention is directed to a medical device that reduces the effects of MRI induced signals to a safe level. The medical device includes a medical device capable of providing medical treatment to a desired tissue region and three orthogonally planar coils, each coil generating a MRI switched gradient field induced current such a combination of the MRI switched gradient field induced currents provide a combined current that is opposite to that which would be induced by the MRI switched gradient fields in the medical device so as to reduce voltages induced by the MRI switched gradient fields to a safe level.

In a further embodiment, the present invention is directed to a medical device that reduces the effects of MRI induced signals to a safe level. The medical device includes a medical device capable of providing medical treatment to a desired tissue region; a plurality of coils, each coil generating a MRI switched gradient field induced current; a sensor to measure a strength of voltages induced by the MRI switched gradient fields; and a switching device, operatively connected to the sensor and plurality of coils, to operatively connect a number of the plurality of coils in response to the measured strength of voltages induced by the MRI switched gradient fields such that a combination of the MRI switched gradient field induced currents produced by the number of operatively connected switches provide a combined current that is opposite to that which would be induced by the MRI switched gradient fields in the medical device so as to reduce voltages induced by the MRI switched gradient fields to a safe level. The coils may be curved in three different spatial directions.

The embodiment may further include an orientation subsystem for changing a spatial orientation of the coil to modify the strength of the MRI switched gradient field induced current.

In a further embodiment, the present invention is directed to a medical device that reduces the effects of MRI induced signals to a safe level. The medical device includes a medical device capable of providing medical treatment to a desired tissue region; three orthogonally planar coil, each coil generating a MRI switched gradient field induced current; a sensor to measure a strength of voltages induced by the MRI switched gradient fields; and a switching device, operatively connected to the sensor and plurality of coils, to operatively connect a number of the plurality of coils in response to the measured strength of voltages induced by the MRI switched gradient fields such that a combination of the MRI switched gradient field induced currents produced by the number of operatively connected switches provide a combined current that is opposite to that which would be induced by the MRI switched gradient fields in the medical device so as to reduce voltages induced by the MRI switched gradient fields to a safe level.

In a further embodiment, the present invention is directed to a medical device that reduces the effects of MRI induced signals to a safe level. The medical device includes a medical device capable of providing medical treatment to a desired tissue region; a plurality of coils, each coil generating a MRI switched gradient field induced current; a transceiver to receive a signal indicating a number of coils to be connected; and a switching device, operatively connected to the transceiver and the coils, to operatively connect a number of the coils in response to the received signal indicating the number of coils to be connected such that a combination of the MRI switched gradient field induced currents produced by the number of operatively connected switches provide a combined current that is opposite to that which would be induced by the MRI switched gradient fields in the medical device electrical lead so as to reduce voltages induced by the MRI switched gradient fields to a safe level. The coils may be curved in three different spatial directions.

The embodiment may further include an orientation subsystem for changing a spatial orientation of the coil to modify the strength of the MRI switched gradient field induced current.

In a further embodiment, the present invention is directed to a medical device that reduces the effects of MRI induced signals to a safe level. The medical device includes a medical device capable of providing medical treatment to a desired tissue region; three orthogonally planar coil, each coil generating a MRI switched gradient field induced current; a transceiver to receive a signal indicating a number of coils to be connected; and a switching device, operatively connected to the transceiver and the coils, to operatively connect a number of the coils in response to the received signal indicating the number of coils to be connected such that a combination of the MRI switched gradient field induced currents produced by the number of operatively connected switches provide a combined current that is opposite to that which would be induced by the MRI switched gradient fields in the medical device electrical lead so as to reduce voltages induced by the MRI switched gradient fields to a safe level.

In a further embodiment, the present invention is directed to a voltage control unit that reduces the effects of MRI induced signals upon a medical device to a safe level. The voltage control unit includes a coil that generates a MRI switched gradient field induced current opposite to that which would be induced by the MRI switched gradient fields in the medical device so as to reduce voltages induced by the MRI switched gradient fields to a safe level. The coil may be curved in three different spatial directions.

The embodiment may further include an orientation subsystem for changing a spatial orientation of the coil to modify the strength of the MRI switched gradient field induced current.

In a further embodiment, the present invention is directed to a voltage control unit that reduces the effects of MRI induced signals upon a medical device to a safe level. The voltage control unit includes a plurality of coils, each coil generating a MRI switched gradient field induced current such a combination of the MRI switched gradient field induced currents provide a combined current that is opposite to that which would be induced by the MRI switched gradient fields in the medical device so as to reduce voltages induced by the MRI switched gradient fields to a safe level. The coils may be curved in three different spatial directions.

The embodiment may further include an orientation subsystem for changing a spatial orientation of the coil to modify the strength of the MRI switched gradient field induced current.

In a further embodiment, the present invention is directed to a voltage control unit that reduces the effects of MRI induced signals upon a medical device to a safe level. The voltage control unit includes three orthogonally planar coils, each coil generating a MRI switched gradient field induced current such a combination of the MRI switched gradient field induced currents provide a combined current that is opposite to that which would be induced by the MRI switched gradient fields in the medical device so as to reduce voltages induced by the MRI switched gradient fields to a safe level.

In a further embodiment, the present invention is directed to a voltage control unit that reduces the effects of MRI induced signals upon a medical device to a safe level. The voltage control unit includes a plurality of coils, each coil generating a MRI switched gradient field induced current; a sensor to measure a strength of voltages induced by the MRI switched gradient fields; and a switching device, operatively connected to the sensor and plurality of coils, to operatively connect a number of the plurality of coils in response to the measured strength of voltages induced by the MRI switched gradient fields such that a combination of the MRI switched gradient field induced currents produced by the number of operatively connected switches provide a combined current that is opposite to that which would be induced by the MRI switched gradient fields in the medical device so as to reduce voltages induced by the MRI switched gradient fields to a safe level. The coils may be curved in three different spatial directions.

The embodiment may further include an orientation subsystem for changing a spatial orientation of the coil to modify the strength of the MRI switched gradient field induced current.

In a further embodiment, the present invention is directed to a voltage control unit that reduces the effects of MRI induced signals upon a medical device to a safe level. The voltage control unit includes three orthogonally planar coil, each coil generating a MRI switched gradient field induced current; a sensor to measure a strength of voltages induced by the MRI switched gradient fields; and a switching device, operatively connected to the sensor and plurality of coils, to operatively connect a number of the plurality of coils in response to the measured strength of voltages induced by the MRI switched gradient fields such that a combination of the MRI switched gradient field induced currents produced by the number of operatively connected switches provide a combined current that is opposite to that which would be induced by the MRI switched gradient fields in the medical device so as to reduce voltages induced by the MRI switched gradient fields to a safe level.

In a further embodiment, the present invention is directed to a voltage control unit that reduces the effects of MRI induced signals upon a medical device to a safe level. The voltage control unit includes a plurality of coils, each coil generating a MRI switched gradient field induced current; a transceiver to receive a signal indicating a number of coils to be connected; and a switching device, operatively connected to the transceiver and the coils, to operatively connect a number of the coils in response to the received signal indicating the number of coils to be connected such that a combination of the MRI switched gradient field induced currents produced by the number of operatively connected switches provide a combined current that is opposite to that which would be induced by the MRI switched gradient fields in the medical device electrical lead so as to reduce voltages induced by the MRI switched gradient fields to a safe level. The coils may be curved in three different spatial directions.

The embodiment may further include an orientation subsystem for changing a spatial orientation of the coil to modify the strength of the MRI switched gradient field induced current.

In a further embodiment, the present invention is directed to a voltage control unit that reduces the effects of MRI induced signals upon a medical device to a safe level. The voltage control unit includes three orthogonally planar coil, each coil generating a MRI switched gradient field induced current; a transceiver to receive a signal indicating a number of coils to be connected; and a switching device, operatively connected to the transceiver and the coils, to operatively connect a number of the coils in response to the received signal indicating the number of coils to be connected such that a combination of the MRI switched gradient field induced currents produced by the number of operatively connected switches provide a combined current that is opposite to that which would be induced by the MRI switched gradient fields in the medical device electrical lead so as to reduce voltages induced by the MRI switched gradient fields to a safe level.

In a further embodiment, the present invention is directed to a lead for medical applications that reduces the effects of MRI induced signals to a safe level. The lead includes two coiled conductive strands forming a spring-like configuration such that current flows over a surface thereof, through contact points between adjacent loops of the coiled conductive strands, and an insulating coating formed over a portion of the two coiled conductive strands such that an inline inductive element is formed, the current flowing along a curvature of the two coiled conductive strands in the insulating coated portion of two coiled conductive strands.

This embodiment may further include a ferrite material positioned in the portion of the two-coiled conductive strands having the insulating coating formed thereon.

In a further embodiment, the present invention is directed to a lead for medical applications that reduces the effects of MRI induced signals to a safe level. The lead includes two coiled conductive strands forming a spring-like configuration such that current flows over a surface thereof, through contact points between adjacent loops of the coiled conductive strands, and an adjustable resistive material formed over a portion of the two coiled conductive strands such that an inline inductive element is formed, the current flowing along a curvature of the two coiled conductive strands in the adjustable resistive material portion of two coiled conductive strands, an inductance of the inline inductive element being adjusted by adjusting the resistive properties of the adjustable resistive material.

This embodiment may further include a ferrite material positioned in the portion of the two-coiled conductive strands having the insulating coating formed thereon.

In a further embodiment, the present invention is directed to a voltage compensation unit for reducing the effects of induced voltages upon a medical device to a safe level. The voltage compensation unit includes a connection device to provide an electrical connection to the medical device; a sensing circuit to voltages of conductive components in the medical device; and a compensation circuit, operatively connected to the sensing circuit and responsive thereto, to provide opposing voltages to the medical device to reduce the effects of induced voltages caused by changing magnetic fields.

This embodiment may also include a power supply, such as a battery or a connection to an external power source. The embodiment may include a second sensing circuit to detect the changing magnetic fields and a compensation circuit, connected to the second sensing circuit and responsive thereto, to synchronize application of the opposing voltages to the medical device with the sensed changing magnetic fields.

In a further embodiment, the present invention is directed to a voltage compensation unit for reducing the effects of induced voltages upon a medical device to a safe level. The voltage compensation unit includes a connection device to provide an electrical connection to the medical device; a sensing circuit to detect changing magnetic fields; and a compensation circuit, operatively connected to the sensing circuit and responsive thereto, to synchronize application of opposing voltages to the medical device with the sensed changing magnetic fields, the opposing voltages reducing the effects of induced voltages caused by the changing magnetic fields.

This embodiment may also include a power supply, such as a battery or a connection to an external power source.

In a further embodiment, the present invention is directed to a voltage compensation unit for reducing the effects of induced voltages upon a medical device to a safe level. The voltage compensation unit includes a connection device to provide an electrical connection to the medical device; a communication circuit, communicatively linked to a MRI system, to receive information associated with a start and end of an application of changing magnetic fields produced by the MRI system; and a compensation circuit, operatively connected to the communication circuit and responsive thereto, to synchronize application of opposing voltages to the medical device with the sensed changing magnetic fields, the opposing voltages reducing the effects of induced voltages caused by the changing magnetic fields.

This embodiment may also include a power supply, such as a battery or a connection to an external power source. The communication circuit may receive information associated with field strengths to be applied by the MRI system, and the compensation circuit would apply opposing voltages in accordance with communicated applied field strengths. The communication circuit may receive the information through electrical wires, coaxial wires, shielded wires, optical fibers, and/or a radio-frequency transmitter/receiver.

In a further embodiment, the present invention is directed to a voltage compensation unit for reducing the effects of induced voltages upon a medical device to a safe level. The voltage compensation unit includes a connection device to provide an electrical connection to the medical device; a communication circuit, communicatively linked to a MRI system, to receive information associated with a start and end of an application of changing magnetic fields produced by the MRI system; and a compensation circuit, operatively connected to the communication circuit and responsive thereto, to apply opposing voltages to the medical device, the opposing voltages reducing the effects of induced voltages caused by the changing magnetic fields.

This embodiment may also include a power supply, such as a battery or a connection to an external power source. The communication circuit may receive information associated with field strengths to be applied by the MRI system, and the compensation circuit would apply opposing voltages in accordance with communicated applied field strengths. The communication circuit may receive the information through electrical wires, coaxial wires, shielded wires, optical fibers, and/or a radio-frequency transmitter/receiver.

While various examples and embodiments of the present invention have been shown and described, it will be appreciated by those skilled in the art that the spirit and scope of the present invention are not limited to the specific description and drawings herein, but extend to various modifications and changes.

What is claimed is:

1. A voltage compensation unit for reducing the effects of induced voltages upon a device to a safe level, comprising:
    a sensing circuit to sense voltages induced in conductive components of the device, the voltages being induced by changing magnetic fields; and
    a compensation circuit, operatively connected to said sensing circuit and responsive thereto, to provide opposing voltages to the device to reduce the effects of induced voltages caused by changing magnetic fields.

2. The voltage compensation unit as claimed in claim 1, further comprising a power supply.

3. The voltage compensation unit as claimed in claim 2, wherein said power supply is a battery.

4. The voltage compensation unit as claimed in claim 1, further comprising:
    a second sensing circuit to detect the changing magnetic fields;
    said compensation circuit, operatively connected to said second sensing circuit and responsive thereto, to synchronize application of the opposing voltages to the device with the sensed changing magnetic fields.

5. The voltage compensation unit as claimed in claim 1, wherein said compensation circuit is shielded from the changing magnetic fields.

6. The voltage compensation unit as claimed in claim 1, further comprising
    a connection device to provide an electrical connection between said sensing circuit and said compensation circuit and the device.

7. The voltage compensation unit as claimed in claim 6, wherein said connection device provides multiple electrical connections between said sensing circuit and said compensation circuit and the device.

8. The voltage compensation unit as claimed in claim 7, wherein said connection device is electrically connected to the device at unequally spaced intervals.

9. The voltage compensation unit as claimed in claim 7, wherein a portion of said multiple electrical connections of said connection device is electrically connected to non-resonance node points of the device.

10. A voltage compensation unit for reducing the effects of induced voltages upon a tissue invasive medical tool to a safe level, comprising:
    a sensing circuit to sense voltages induced in conductive components of the medical tool, the voltages being induced by changing magnetic fields;
    a compensation circuit, operatively connected to said sensing circuit and responsive thereto, to provide opposing voltages to the medical tool to reduce the effects of induced voltages caused by changing magnetic fields; and
    a connection device to provide an electrical connection between said sensing circuit and said compensation circuit and the medical tool.

11. The voltage compensation unit as claimed in claim 10, wherein said connection device provides multiple electrical connections along the medical tool.

12. The voltage compensation unit as claimed in claim 11, wherein said connection device is electrically connected to the medical tool at unequally spaced intervals.

13. The voltage compensation unit as claimed in claim 11, wherein a portion of said multiple electrical connections of said connection device is electrically connected to non-resonance node points of the medical tool.

14. The voltage compensation unit as claimed in claim 10, further comprising:
    a second sensing circuit to detect changing magnetic fields;
    said compensation circuit, operatively connected to said second sensing circuit and responsive thereto, to synchronize application of opposing voltages to the medical tool with the sensed changing magnetic fields, said opposing voltages reducing the effects of induced voltages caused by the changing magnetic fields.

15. The voltage compensation unit as claimed in claim 10, wherein said compensation circuit is shielded from the changing magnetic fields.

16. A voltage compensation unit for reducing the effects of induced voltages upon a device to a safe level, comprising:
    a communication circuit, communicatively linked to a MRI system, to receive, from the MRI system, information associated with a start and end of an application of changing magnetic fields produced by the MRI system; and
    a compensation circuit, operatively connected to said communication circuit and responsive thereto, to synchronize application of opposing voltages to the device with the start and end of the application of the changing magnetic fields produced by the MRI system, said opposing voltages reducing the effects of induced voltages caused by the changing magnetic fields.

17. The voltage compensation unit as claimed in claim 16, further comprising
    a connection device to provide an electrical connection between said compensation circuit and the device.

18. The voltage compensation unit as claimed in claim 17, wherein said connection device provides multiple electrical connections between said compensation circuit and the device.

19. The voltage compensation unit as claimed in claim 18, wherein said connection device is electrically connected to the device at unequally spaced intervals.

20. The voltage compensation unit as claimed in claim 18, wherein a portion of said multiple electrical connections of said connection device is electrically connected to non-resonance node points of the device.

21. The voltage compensation unit as claimed in claim 16, wherein said communication circuit receives information associated with MRI scan pulse sequences to be applied by the MRI system;
said compensation circuit applies opposing voltages in accordance with communicated applied MRI scan pulse sequences.

22. The voltage compensation unit as claimed in claim 16, wherein said communication circuit receives information associated with timing of application of fields and pulse shapes thereof to be applied by the MRI system;
said compensation circuit applies opposing voltages in accordance with communicated timing of applied fields and pulse shapes thereof.

23. The voltage compensation unit as claimed in claim 16, wherein said communication circuit receives information associated with pulse shapes of a field to be applied by the MRI system;
said compensation circuit applies opposing voltages in accordance with communicated applied pulse shapes.

24. The voltage compensation unit as claimed in claim 16, wherein said communication circuit receives the information through electrical wires.

25. The voltage compensation unit as claimed in claim 16, wherein said communication circuit receives the information through coaxial wires.

26. The voltage compensation unit as claimed in claim 16, wherein said communication circuit receives the information through shielded wires.

27. The voltage compensation unit as claimed in claim 16, wherein said communication circuit receives the information through optical fibers.

28. The voltage compensation unit as claimed in claim 16, wherein said communication circuit receives the information through a radio-frequency transmitter/receiver.

29. The voltage compensation unit as claimed in claim 16, wherein said communication circuit receives the information through an acoustic transmitter/receiver.

30. A voltage compensation unit for reducing the effects of induced voltages upon a device to a safe level, comprising:
a communication circuit, communicatively linked to a MRI system, to receive, from the MRI system, information associated with a start and end of an application of changing magnetic fields produced by the MRI system; and
a compensation circuit, operatively connected to said communication circuit and responsive thereto, to apply opposing voltages to the device, said opposing voltages reducing the effects of induced voltages caused by the changing magnetic fields.

31. The voltage compensation unit as claimed in claim 30, further comprising
a connection device to provide an electrical connection between said compensation circuit and the device.

32. The voltage compensation unit as claimed in claim 31, wherein said connection device provides multiple electrical connections between said compensation circuit and the device.

33. The voltage compensation unit as claimed in claim 32, wherein said connection device is electrically connected to the device at unequally spaced intervals.

34. The voltage compensation unit as claimed in claim 32, wherein a portion of said multiple electrical connections of said connection device is electrically connected to non-resonance node points of the device.

35. The voltage compensation unit as claimed in claim 30, wherein said communication circuit receives information associated with MRI scan pulse sequences to be applied by the MRI system;
said compensation circuit applies opposing voltages in accordance with communicated applied MRI scan pulse sequences.

36. The voltage compensation unit as claimed in claim 30, wherein said communication circuit receives information associated with timing of application of fields and pulse shapes thereof to be applied by the MRI system;
said compensation circuit applies opposing voltages in accordance with communicated timing of applied fields and pulse shapes thereof.

37. The voltage compensation unit as claimed in claim 30, wherein said communication circuit receives information associated with pulse shapes of a field to be applied by the MRI system;
said compensation circuit applies opposing voltages in accordance with communicated applied pulse shapes.

38. The voltage compensation unit as claimed in claim 30, wherein said communication circuit receives the information through electrical wires.

39. The voltage compensation unit as claimed in claim 30, wherein said communication circuit receives the information through coaxial wires.

40. The voltage compensation unit as claimed in claim 30, wherein said communication circuit receives the information through shielded wires.

41. The voltage compensation unit as claimed in claim 30, wherein said communication circuit receives the information through optical fibers.

42. The voltage compensation unit as claimed in claim 30, wherein said communication circuit receives the information through a radio-frequency transmitter/receiver.

43. The voltage compensation unit as claimed in claim 30, wherein said communication circuit receives the information through an acoustic transmitter/receiver.

44. A voltage compensation unit for reducing the effects of induced voltages upon a device having a single wire line, the single wire line having a balanced characteristic impedance, comprising:
a tunable compensation circuit, operatively connected to the wire line, to apply variable supplemental impedance to the wire line, said variable supplemental impedance causing the characteristic impedance of the wire line to become unbalanced, thereby reducing the effects of induced voltages caused by changing magnetic fields.

45. The voltage compensation unit as claimed in claim 44, wherein said tunable compensation circuit is a plurality of variable capacitors.

46. The voltage compensation unit as claimed in claim 44, wherein said tunable compensation circuit is a balun.

47. The voltage compensation unit as claimed in claim 44, wherein said tunable compensation circuit is an IF amplifier, said IF amplifier automatically applying supplemental impedance to the wire line to cause the characteristic impedance of the wire line to become unbalanced.

48. The voltage compensation unit as claimed in claim 44, wherein said tunable compensation circuit is manually tunable to change an amount of said supplemental impedance being applied to the wire line.

49. The voltage compensation unit as claimed in claim 2, wherein said power supply is a connection to an external power source.

* * * * *